(12) United States Patent
Justis et al.

(10) Patent No.: US 8,128,699 B2
(45) Date of Patent: Mar. 6, 2012

(54) SPINAL IMPLANT AND METHODS OF IMPLANTATION AND TREATMENT

(75) Inventors: Jeff R. Justis, Germantown, TN (US); Hai H. Trieu, Cordova, TN (US); Dimitri K. Protopsaltis, Memphis, TN (US); Jeffrey H. Nycz, Warsaw, IN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 435 days.

(21) Appl. No.: 12/403,585

(22) Filed: Mar. 13, 2009

(65) Prior Publication Data

US 2010/0234954 A1 Sep. 16, 2010

(51) Int. Cl.
*A61F 2/44* (2006.01)

(52) U.S. Cl. ............ 623/17.11; 623/17.16; 600/12

(58) Field of Classification Search .......... 606/246–249; 623/17.11–17.16, 16.11; 600/12
See application file for complete search history.

(56) References Cited

U.S. PATENT DOCUMENTS

| | | | |
|---|---|---|---|
| 5,443,524 A | 8/1995 | Sawamura et al. | |
| 5,571,205 A | 11/1996 | James | |
| 5,888,212 A | 3/1999 | Petrofsky et al. | |
| 5,893,891 A | 4/1999 | Zahedi | |
| 6,074,365 A * | 6/2000 | Hahndel et al. | 604/151 |
| 6,113,542 A | 9/2000 | Hyman et al. | |
| 6,132,633 A | 10/2000 | Carlson | |
| 6,203,717 B1 | 3/2001 | Munoz et al. | |
| 6,423,098 B1 | 7/2002 | Biedermann | |
| 6,443,993 B1 | 9/2002 | Koniuk | |
| 6,478,825 B1 | 11/2002 | Winterbottom et al. | |
| 6,511,512 B2 | 1/2003 | Phillips et al. | |
| 6,517,585 B1 | 2/2003 | Zahedi et al. | |
| 6,610,101 B2 | 8/2003 | Herr et al. | |
| 6,663,673 B2 | 12/2003 | Christensen | |
| 6,692,495 B1 | 2/2004 | Zacouto | |
| 6,702,858 B2 | 3/2004 | Christensen | |
| 6,740,125 B2 | 5/2004 | Mosler | |
| 6,755,870 B1 | 6/2004 | Biedermann et al. | |
| 6,764,520 B2 | 7/2004 | Deffenbaugh et al. | |
| 6,835,207 B2 | 12/2004 | Zacouto et al. | |
| 6,875,241 B2 | 4/2005 | Christensen | |
| 6,875,242 B2 | 4/2005 | Christensen | |
| 6,882,086 B2 | 4/2005 | Kornbluh et al. | |
| 6,886,819 B2 | 5/2005 | Kintz et al. | |

(Continued)

OTHER PUBLICATIONS

Buford, Get ready for Smart Implants, Product Development in Orthopedics, Orthopedics, Smart Implants, Dec. 25, 2007, pp. 1-9.

(Continued)

*Primary Examiner* — Eduardo C Robert
*Assistant Examiner* — Christina Negrelli

(57) ABSTRACT

A spinal implant is provided that includes a first component for engaging a first vertebra, a second component for engaging a second vertebrae, and a damping member is positioned therebetween. The damping member has at least two chambers connected by an opening. A fluid is disposed within the chambers such that compression of the first and second components towards one another causes the fluid to be displaced from one of the chambers to another chamber through an opening. The opening has a reduced size relative to the chambers to restrict the flow of the fluid between the chambers and provide a dampening effect. In some instances, the rheologic properties of the fluid positioned within the chambers are dependent upon the strength a magnetic field passing through the fluid. In other aspects of the present disclosure, prosthetic devices, intervertebral implants, spinal systems, implantation methods, and treatment methods are provided.

17 Claims, 10 Drawing Sheets

U.S. PATENT DOCUMENTS

| | | |
|---|---|---|
| 6,887,279 B2 | 5/2005 | Phillips et al. |
| 6,902,585 B2 | 6/2005 | Hikichi |
| 6,969,365 B2 | 11/2005 | Scorvo |
| 7,029,500 B2 | 4/2006 | Martin |
| 7,031,772 B2 | 4/2006 | Condie et al. |
| 7,066,957 B2 | 6/2006 | Graf |
| 7,087,184 B2 | 8/2006 | Kintz et al. |
| 7,101,487 B2 | 9/2006 | Hsu et al. |
| 7,235,102 B2 | 6/2007 | Ferree et al. |
| 2004/0024460 A1 | 2/2004 | Ferree |
| 2004/0044410 A1 | 3/2004 | Ferree et al. |
| 2005/0015150 A1 | 1/2005 | Lee |
| 2005/0113928 A1 | 5/2005 | Cragg et al. |
| 2005/0113929 A1 | 5/2005 | Cragg et al. |
| 2005/0192674 A1 | 9/2005 | Ferree |
| 2005/0283257 A1 | 12/2005 | Bisbee et al. |
| 2006/0079898 A1 | 4/2006 | Ainsworth et al. |
| 2006/0136061 A1 | 6/2006 | Navarro et al. |
| 2006/0142860 A1 | 6/2006 | Navarro et al. |
| 2006/0149377 A1 | 7/2006 | Navarro et al. |
| 2006/0149383 A1 | 7/2006 | Arnin et al. |
| 2006/0149384 A1 | 7/2006 | Navarro et al. |
| 2006/0155385 A1 | 7/2006 | Martin |
| 2006/0178753 A1 * | 8/2006 | Hsu et al. .......... 623/26 |
| 2006/0259143 A1 | 11/2006 | Navarro et al. |
| 2006/0259145 A1 | 11/2006 | Navarro et al. |
| 2006/0259146 A1 | 11/2006 | Navarro et al. |
| 2007/0168036 A1 | 7/2007 | Ainsworth et al. |
| 2008/0046082 A1 | 2/2008 | Lee |
| 2008/0065076 A1 | 3/2008 | Cragg et al. |
| 2009/0234456 A1 * | 9/2009 | Nycz .......... 623/17.16 |

OTHER PUBLICATIONS

Buford, The Future of Orthopedics is Smart Implants, Product Development in Orthopedics, Orthopedics, Smart Implants, Aug. 29, 2007, pp. 1-4.

Theken eDisc, 2006, 1 page.

McGraw, A Curious Fluid and an Electric Jolt Deliver a Magic Carpet Ride, The New York Times, Feb. 21, 2005, 2 pages.

U.S. Appl. No. 12/048,627, filed Mar. 14, 2008.

* cited by examiner

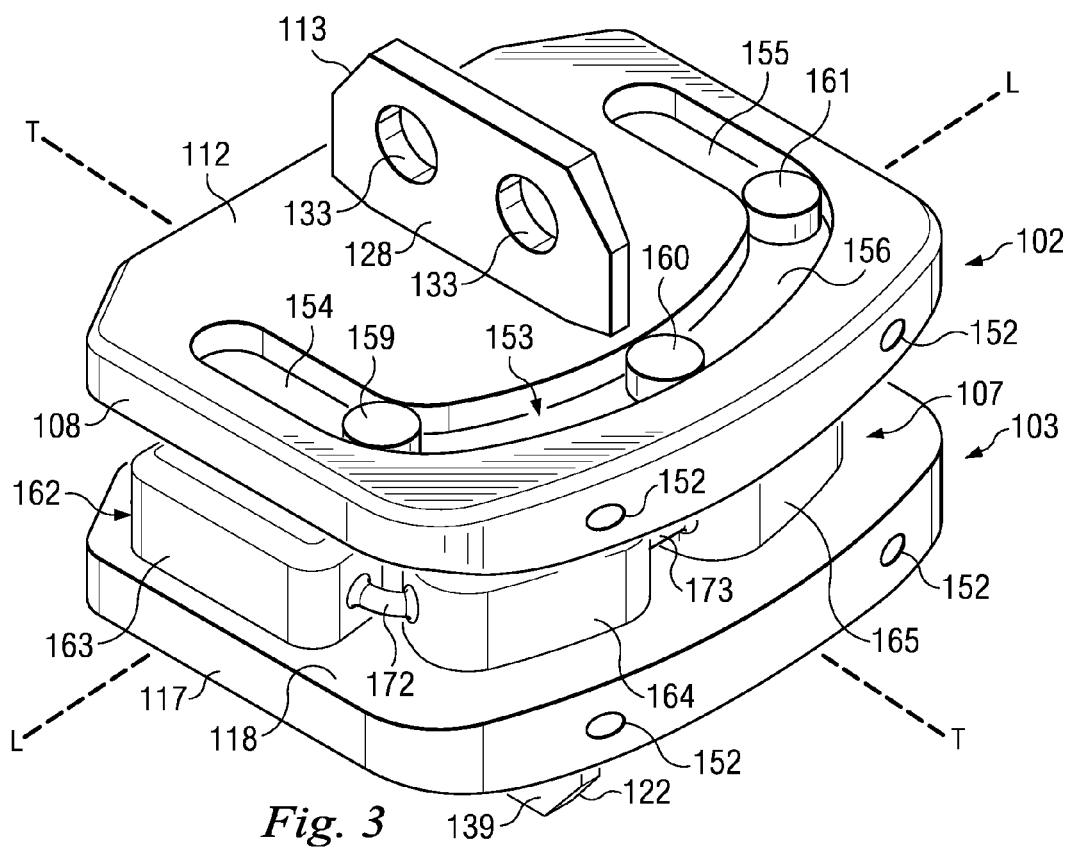

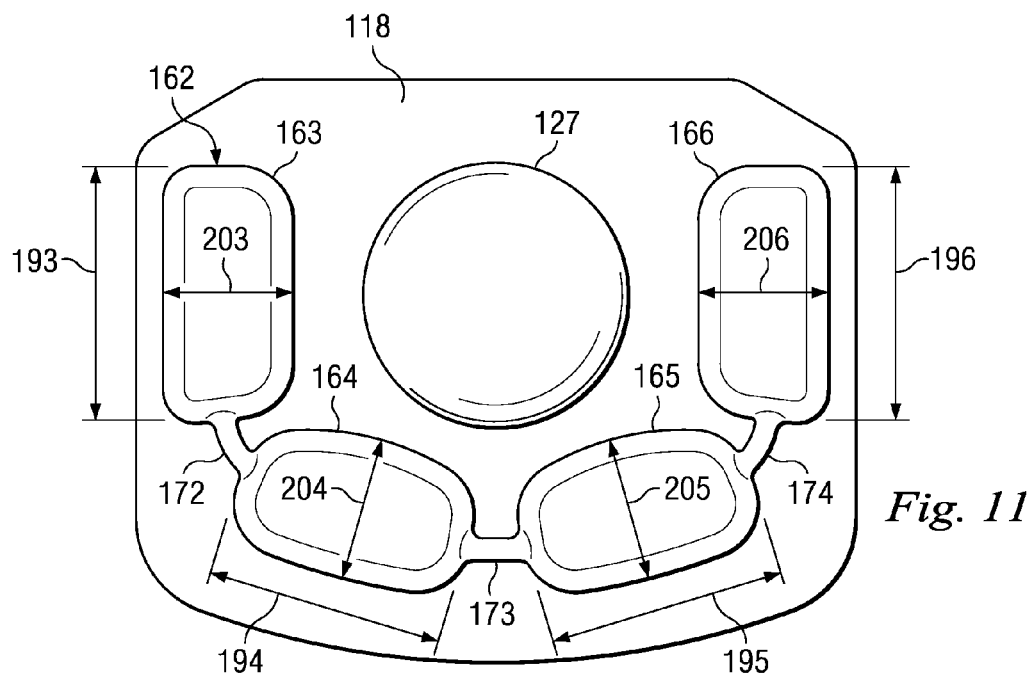
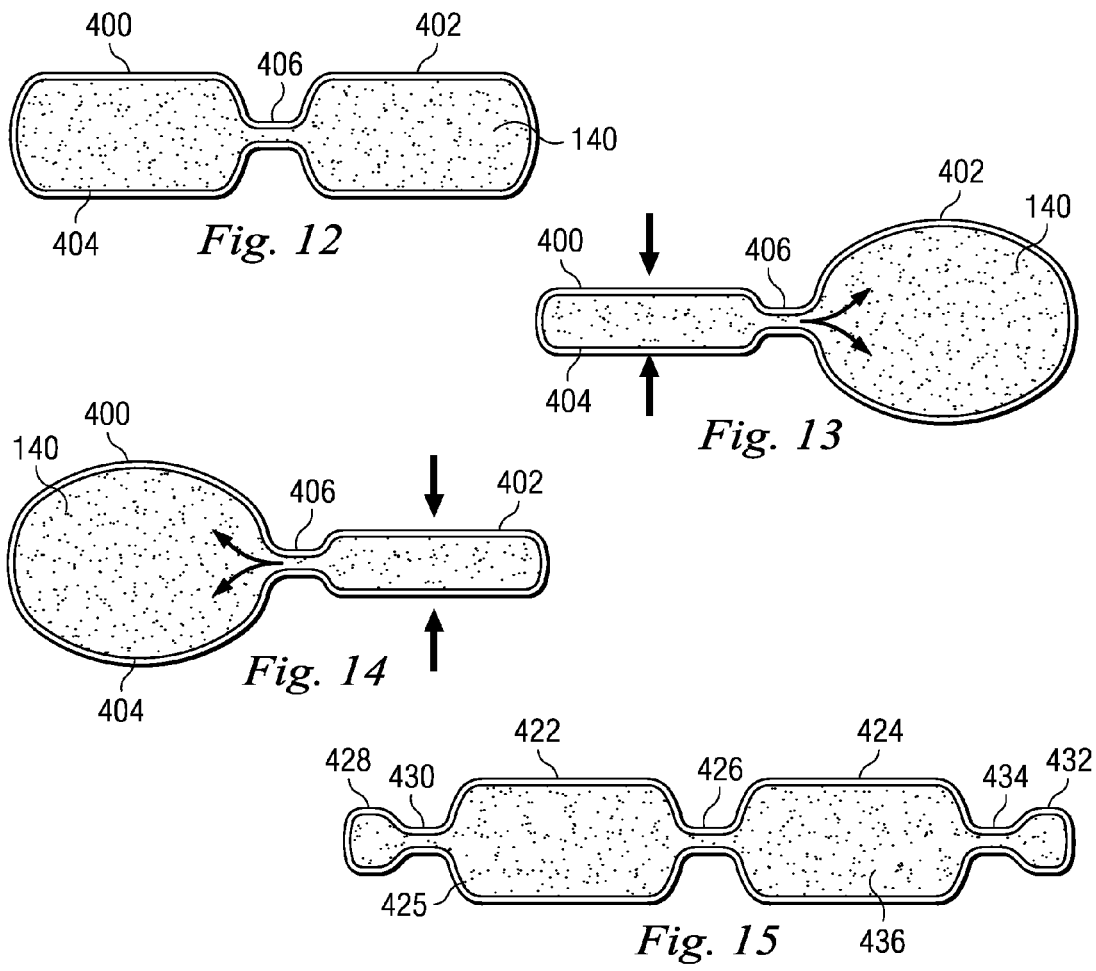
Fig. 11
Fig. 12
Fig. 13
Fig. 14
Fig. 15

SPINAL IMPLANT AND METHODS OF IMPLANTATION AND TREATMENT

TECHNICAL FIELD

Embodiments of the present disclosure relate generally to spinal implants and associated methods of implantation and treatment.

BACKGROUND

Within the spine, the intervertebral disc functions to stabilize and distribute forces between vertebral bodies. It comprises a nucleus pulposus which is surrounded and confined by the annulus fibrosis.

Intervertebral discs are prone to injury and degeneration. For example, herniated discs typically occur when normal wear or exceptional strain causes a disc to rupture. Degenerative disc disease typically results from the normal aging process, in which the tissue gradually loses its natural water and elasticity, causing the degenerated disc to shrink and possibly rupture. Intervertebral disc injuries and degeneration may be treated by fusion of adjacent vertebral bodies or by replacing the intervertebral disc with an implant, also known as a prosthesis or prosthetic device. Generally, fusion of the adjacent vertebral bodies prevents movement between the adjacent vertebrae and the range of motion provided by the natural intervertebral disc. Some implants, on the other hand, preserve at least some of the range of motion provided by the natural intervertebral disc.

Although existing devices and methods associated with intervertebral implants have been generally adequate for their intended purposes, they have not been entirely satisfactory in all respects. The devices and methods in this disclosure overcome one or more of the shortcomings of the prior art.

SUMMARY

In one aspect, a spinal implant is provided.

In a further aspect, an intervertebral implant for positioning between an upper vertebra and a lower vertebra is provided. The intervertebral implant comprises an upper endplate for engaging the upper vertebra and a lower endplate for engaging the lower vertebra. A damping member is disposed between the upper and lower endplates. The damping member includes a plurality of chambers having a material disposed therein. The material has a viscosity that is dependent on a magnetic field strength. The intervertebral implant also includes a plurality of permanent magnets disposed in at least one of the upper endplate and the lower endplate. The plurality of permanent magnets generate magnetic fields for controlling the viscosity of the material disposed in the plurality of chambers of the damping member.

In some instances, at least two of the plurality of chambers are connected by an opening that restricts a flow of the material between the at least two of the plurality of chambers. In that regard, in some embodiments, at least one of the plurality of magnets is disposed adjacent to the opening to produce a magnetic field through the opening in order to control the viscosity of the material within the opening. In some instances, at least one of the upper endplate and the lower endplate includes a recess for receiving the magnet disposed adjacent to the opening. In that regard, the magnet disposed adjacent to the opening is movable within the recess between a first position where the magnetic field through the opening has a first strength and a second position where the magnetic field through the opening has a second strength greater than the first strength. In some instances, each of the plurality of chambers is connected to at least one other of the plurality of chambers via an opening having a reduced inner profile relative to an inner profile of the connected chambers. In that regard, in some instances, the reduced inner profile of the opening restricts a flow of the material between the connected chambers. Also, in that regard, in some instances, at least one of the plurality of magnets is disposed adjacent to each opening to produce a magnetic field through the opening in order to control the viscosity of the material within each opening. In some instances, the plurality of magnets are disposed in a fixed orientation within a plate. Further, in some instances at least one of the upper endplate and the lower endplate includes a recess for receiving the plate. In that regard, in some instances, the fixed orientation of the plurality of magnets generally corresponds to an arrangement of a plurality of openings connecting the plurality of chambers such that each of the plurality of magnets is positioned adjacent one of the plurality of openings. Further, the plate is slidable along the recess so that a distance between each of the plurality of magnets and the corresponding openings is variable in order to adjust a strength of the magnetic field through each opening, in some instances.

In a further aspect, a prosthetic device for a spinal joint is provided. The prosthetic devices comprises a first component sized and shaped for engaging a first bony portion of the spinal joint and a second component sized and shaped for engaging a second bony portion of the spinal joint. The second component is in articulating engagement with the first component. A bladder system is positioned between the first and second components. The bladder system comprises a plurality of flexible bladders and at least one orifice extending from each of the plurality of bladders to at least one other of the plurality of bladders. Each of the plurality of bladders contains a fluid. Also, the at least one orifice has a reduced inner diameter relative to an inner diameter of the plurality of bladders such that a flow of fluid between the bladders connected by the at least one orifice is restricted.

In some instances, the first and second components are in articulating engagement via a ball-and-socket joint. Also, in some instances, the bladder system generally surrounds the ball-and-socket joint. In some instances, the fluid is selected from the group of biocompatible fluids comprising water, saline, polyethylene glycol, glycerol, plasma extender, and hydrocarbon solvents. In some instances, the fluid is selected from the group of biocompatible fluids comprising magnetorheologic fluids, ferrofluids, and electrorheologic fluids. In that regard, in some instances, the prosthetic device includes at least one field generating component for defining a rheological behavior of the fluid.

In another aspect, a spinal implant is provided. The spinal implant comprises a first component that includes a first engagement surface for engaging a first vertebra, and a second component that includes a second engagement surface for engaging a second vertebra. A damping member is positioned between the first and second components. Also, the damping member comprises at least two chambers connected by at least one opening. A fluid is disposed within the chambers of the damping member such that compression of the first and second components towards one another causes the fluid to be displaced from one of the chambers to another of the chambers through the at least one opening. In addition, the at least one opening has a reduced size relative to the chambers to restrict the flow of the fluid between the chambers and provide a dampening effect.

In some instances, the fluid comprises magnetically sensitive particles such that a rheologic behavior of the fluid is dependent on a magnetic field passing through the fluid. In some embodiments, the prosthetic device comprises a magnetic source for generating a magnetic field for controlling the rheologic behavior of the fluid. In that regard, in some instances, the magnetic source is at least one permanent magnet. In other instances, the magnetic source comprises electronics that produce an electromagnetic field. In some embodiments, the damping member comprises a strut. In that regard, in some instances, a first portion of the strut is fixedly attached to the first component and a second portion of the strut is fixedly attached to the second component.

In some instances, methods of implanting spinal devices are disclosed. Further, in some instances methods of treating a patient with a spinal device are disclosed.

Additional aspects and features of the present disclosure will be apparent from the detailed description, drawings, and claims as set forth herein.

BRIEF DESCRIPTION OF THE DRAWINGS

FIG. 3 is a diagrammatic perspective view of the intervertebral implant shown in FIG. 2.

FIG. 4 is a diagrammatic front perspective view of the intervertebral implant shown in FIGS. 2 and 3.

FIG. 11 is a diagrammatic top view of the lower portion of the intervertebral implant shown in FIGS. 9 and 10.

FIG. 12 is a diagrammatic front view of two exemplary chambers of a multi-chamber support of the intervertebral implant shown in FIGS. 2-4 illustrated in a neutral position.

FIG. 13 is another diagrammatic front view of the two exemplary chambers of the multi-chamber support of the intervertebral implant similar to that of FIG. 12, but showing the bladders in a first articulation position.

FIG. 14 is another diagrammatic front view of two exemplary chambers of the multi-chamber support of the intervertebral implant similar to that of FIGS. 12 and 13, but showing the bladders in a second articulation position.

FIG. 15 is a diagrammatic front view of a multi-chamber support, according to an alternative embodiment of the present disclosure.

DETAILED DESCRIPTION

Figure 1:
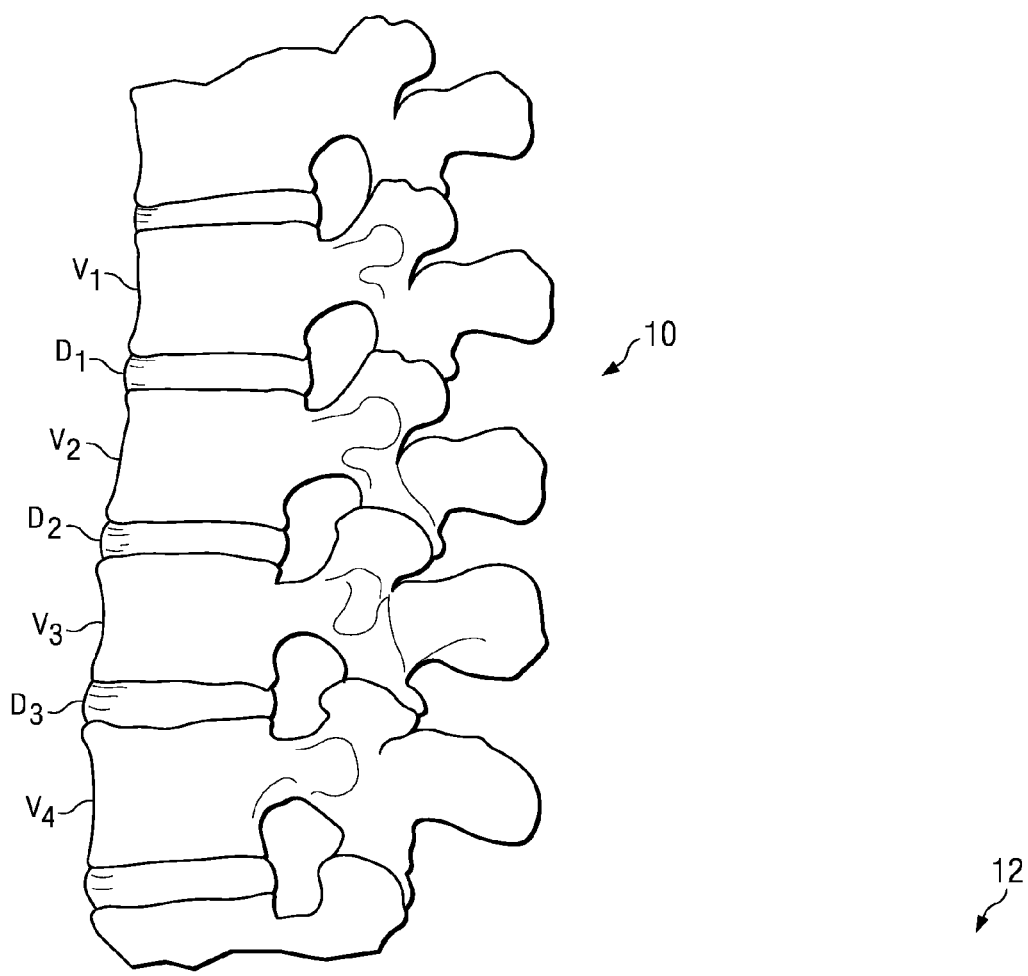
FIG. 1 is a diagrammatic side elevation view of an adult human vertebral column.

For the purpose of promoting an understanding of the principles of the present disclosure, reference is made to the specific embodiments illustrated in the drawings, and specific language is used to describe the embodiments. It is nevertheless understood that no limitation of the scope of the present disclosure is intended. Any alterations and further modifications of the described embodiments, and any further applications of the principles of the present disclosure as described herein, are fully contemplated, as would occur to one skilled in the art to which the invention relates.

FIG. 1 illustrates a lateral view of a portion of a spinal column 10, illustrating a group of adjacent upper and lower vertebrae V1, V2, V3, V4 separated by natural intervertebral discs D1, D2, D3. Although the illustration generally depicts the lumbar region, it is understood that the devices, systems, and methods of this disclosure also can be applied to all regions of the vertebral column, including the cervical and thoracic regions. A vertebral joint comprises two adjacent vertebrae separated by an intervertebral disc.

Figure 2:
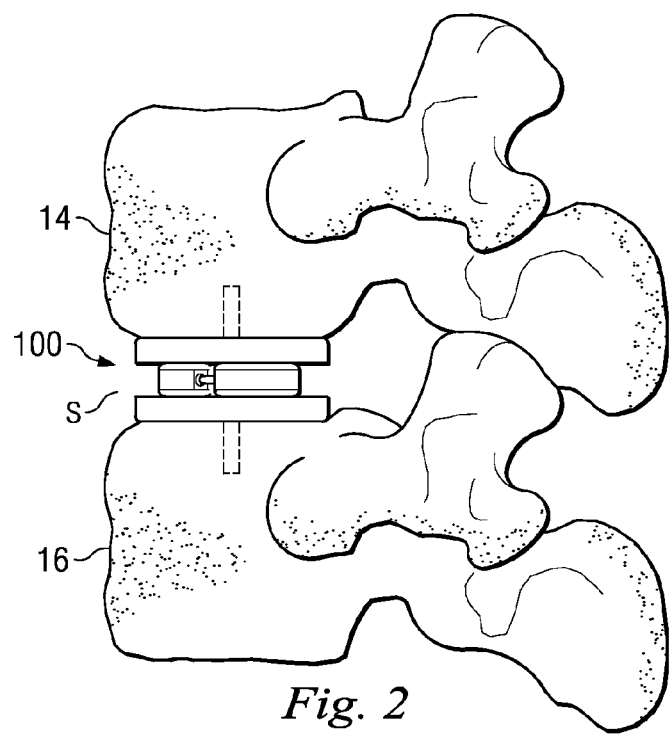
FIG. 2 is a diagrammatic side elevation view of a portion of the vertebral column of FIG. 1, depicting an intervertebral implant according to one embodiment of the present disclosure positioned between two adjacent vertebrae.

FIG. 2 is a diagrammatic side elevation view of a portion 12 of the vertebral column of FIG. 1. The portion 12 includes an exemplary vertebral joint, having an upper vertebra 14 and a lower vertebra 16. Also, the portion 12 has a disc space S between the upper and lower vertebrae 14, 16. The disc space S is created by removal of a natural intervertebral disc (not shown) that is normally disposed between the upper and lower vertebrae 14, 16. In this illustration, an intervertebral implant 100 is disposed in the disc space S.

Generally, the intervertebral implant 100 is sized to fit within the disc space S in a manner similar to that of a natural intervertebral disc, as shown in FIG. 2. The intervertebral implant 100 provides support and stabilization to the vertebrae 14, 16. In addition, the intervertebral implant 100 allows the upper vertebra 14 to move relative to the lower vertebra 16 to preserve at least some movement in the vertebral joint 12. In some instances, the intervertebral implant 100 provides cushioning and damping to control the amount or degree of movement between the vertebrae 14, 16 and/or the amount of support and cushioning provided to the vertebral joint 12. Further, in some embodiments the intervertebral implant 100 has an adjustable stiffness and damping in order to provide a desired amount of motion and support to the vertebral joint 12. In some instances, the intervertebral implant 100 provides variable damping to control the amount or degree of movement between the vertebrae 14, 16 and/or the amount of support provided to the vertebral joint 12. Further, in some embodiments the intervertebral implant 100 continuously self-adjusts the damping that it provides, as necessary, to maintain a desired amount of motion and support to the vertebral joint 12. In some embodiments, the damping of the intervertebral implant 100 is adjusted in the sagittal, axial, and/or coronal planes to provide the desired amount of motion and/or support in the respective plane(s).

Figure 5:
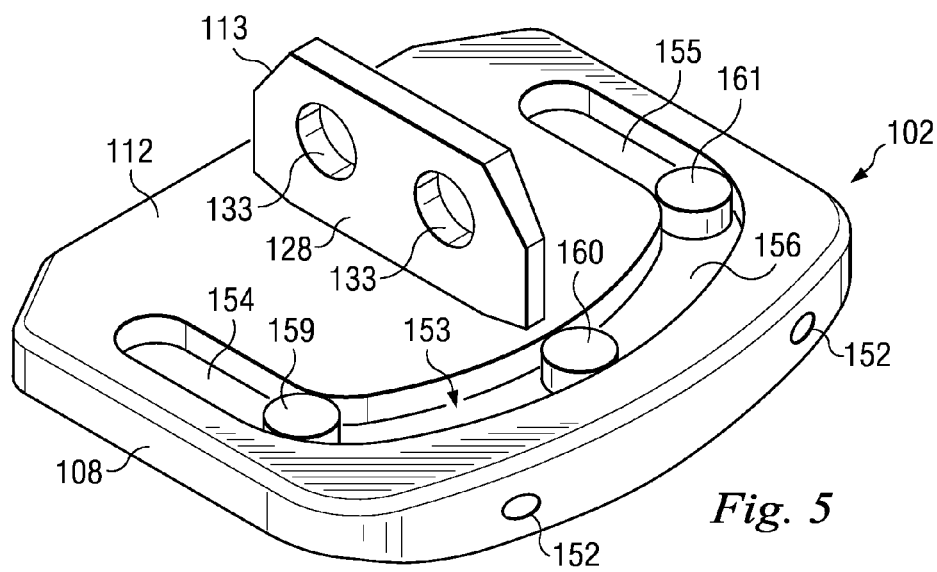
FIG. 5 is a diagrammatic perspective view of an upper portion of the intervertebral implant shown in FIGS. 2-4.
Figure 6:
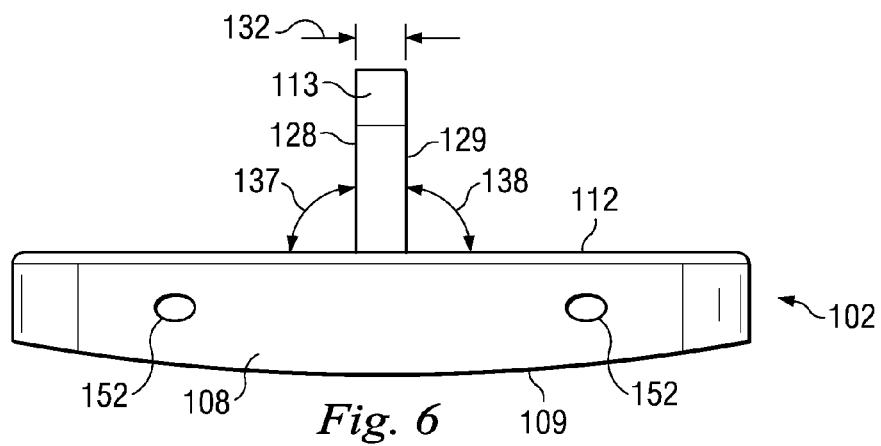
FIG. 6 is a diagrammatic front view of the upper portion of the intervertebral implant shown in FIG. 5.
Figure 7:
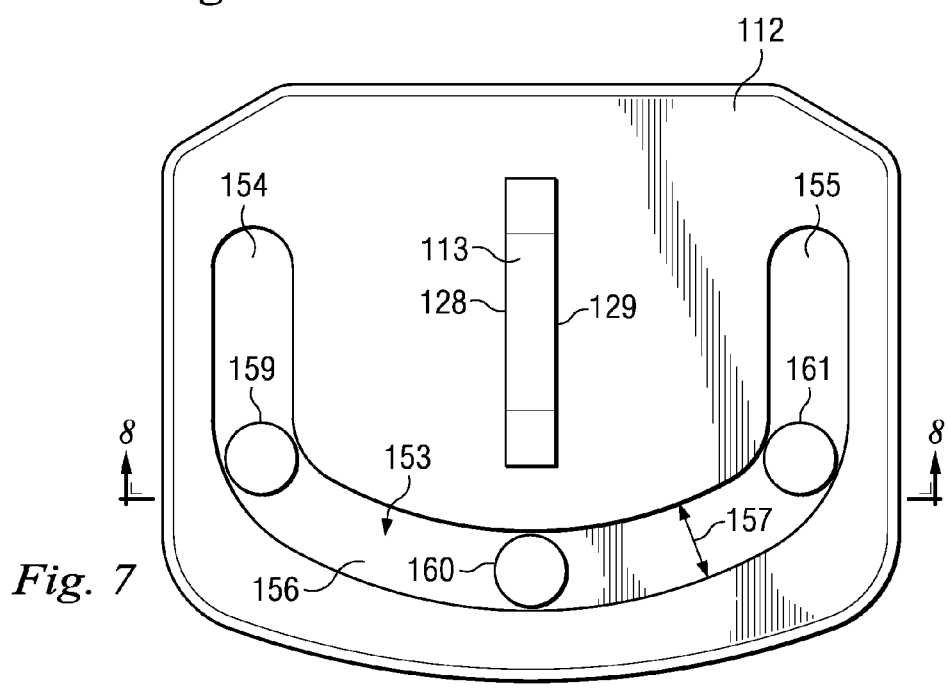
FIG. 7 is a diagrammatic top view of the upper portion of the intervertebral implant shown in FIGS. 5 and 6.
Figure 8:
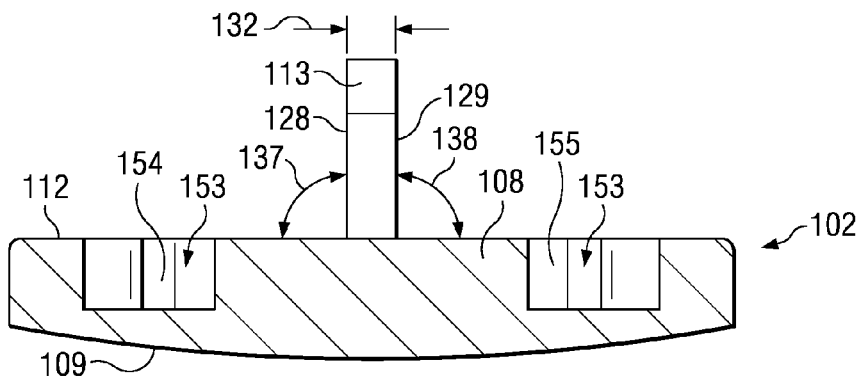
FIG. 8 is a diagrammatic cross section view of the upper portion of the intervertebral implant shown in FIGS. 5-7, taken along section line 8-8 shown in FIG. 7.
Figure 9:
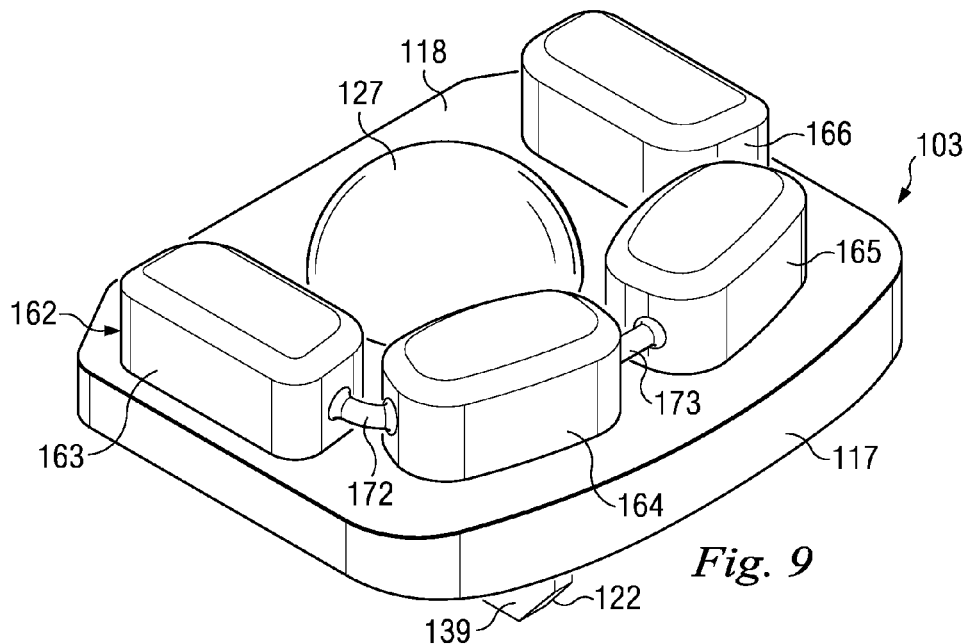
FIG. 9 is a diagrammatic perspective view of a lower portion of the intervertebral implant shown in FIGS. 2-4.
Figure 10:
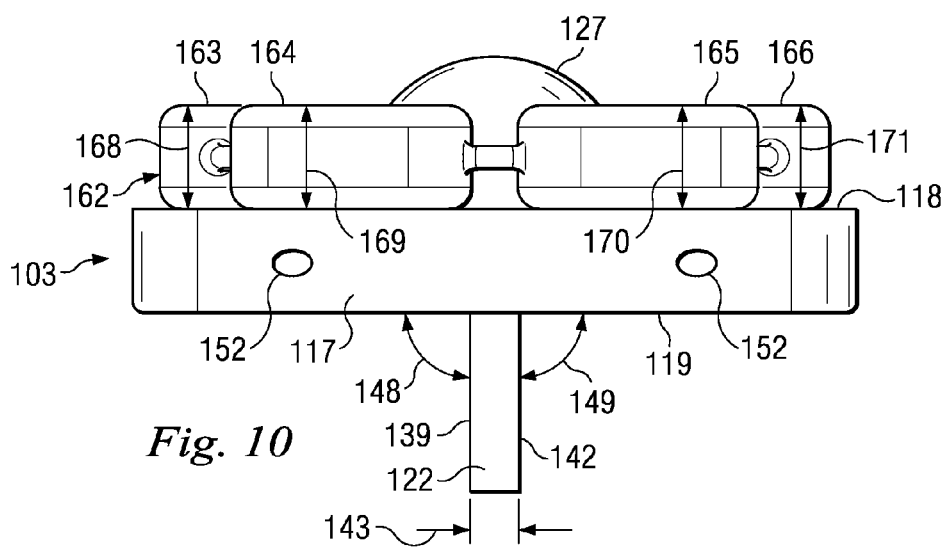
FIG. 10 is a diagrammatic front view of the lower portion of the intervertebral implant shown in FIG. 9.

Referring generally to FIGS. 2-14, the intervertebral implant 100 will be discussed in greater detail. FIG. 2 is a diagrammatic side elevation view of a portion of the vertebral column of FIG. 1, depicting an intervertebral implant according to one embodiment of the present disclosure positioned between two adjacent vertebrae. FIG. 3 is a diagrammatic perspective view of the intervertebral implant shown in FIG. 2. FIG. 4 is a diagrammatic front perspective view of the intervertebral implant shown in FIGS. 2 and 3. FIG. 5 is a diagrammatic perspective view of an upper portion of the intervertebral implant shown in FIGS. 2-4. FIG. 6 is a diagrammatic front view of the upper portion of the intervertebral implant shown in FIG. 5. FIG. 7 is a diagrammatic top view of the upper portion of the intervertebral implant shown in FIGS. 5 and 6. FIG. 8 is a diagrammatic cross section view of the upper portion of the intervertebral implant shown in FIGS. 5-7, taken along section line 8-8 shown in FIG. 7. FIG. 9 is a diagrammatic perspective view of a lower portion of the intervertebral implant shown in FIGS. 2-4. FIG. 10 is a diagrammatic front view of the lower portion of the intervertebral implant shown in FIG. 9. FIG. 11 is a diagrammatic top view of the lower portion of the intervertebral implant shown in FIGS. 9 and 10. FIG. 12 is a diagrammatic front view of two exemplary chambers of a multi-chamber support of the intervertebral implant shown in FIGS. 2-4 illustrated in a neutral position. FIG. 13 is another diagrammatic front view of the two exemplary chambers of the multi-chamber support of the intervertebral implant similar to that of FIG. 12, but showing the chambers in a first articulation position. FIG. 14 is another diagrammatic front view of two exemplary chambers of the multi-chamber support of the intervertebral implant similar to that of FIGS. 12 and 13, but showing the chambers in a second articulation position.

Referring to FIG. 3, shown therein is a diagrammatic perspective view of the intervertebral implant 100 shown in FIG. 2. The intervertebral implant 100 extends generally along a longitudinal axis L and includes an upper portion 102, a lower portion 103, and an articulating central portion 107. The upper and lower portions 102, 103 and the articulating portion 107 cooperate to form the intervertebral implant 100, which is sized and configured for disposition within an intervertebral space between a pair of vertebral bodies, such as the intervertebral space S between the adjacent vertebrae 14, 16. The upper portion 102 includes an upper support plate 108 having an articulating surface 109 and an opposing engagement surface 112. The engagement surface 112 includes one or more features for enhancing the engagement with the upper vertebra 14 in some embodiments. In the illustrated embodiment, an engagement structure 113 extends from the engagement surface 112. Similarly, the lower portion 103 includes a support plate 117 having an articulating surface 118 and an opposing engagement surface 119. The engagement surface 119 includes one or more features for enhancing the engagement with the upper vertebra 14 in some embodiments. An engagement structure 122 extends from the engagement surface 119.

In the current embodiment, the support plates 108, 117 are sized and shaped to substantially correspond to the size and shape of the adjacent vertebra 14, 16. In other embodiments, the support plates 108, 117 are sized and shaped to correspond to only a portion of the vertebrae 14, 16. For example, in one alternative embodiment the support plates 108, 117 are sized and shaped for use in a bilateral procedure. In some embodiments, the upper support plate 108 and the lower support plate 117 have different sizes.

The upper and lower support plates 108, 117 are formed of suitable biocompatible materials. In instances, metals such as cobalt-chromium alloys, titanium alloys, nickel titanium alloys, and/or stainless steel alloys are utilized. Ceramic materials such as aluminum oxide or alumnia, zirconium oxide or zirconia, compact of particulate diamond, and/or pyrolytic carbon are suitable in some instances. In some embodiments, polymer materials are utilized, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE.

Further, the engagement surfaces 112, 119 of the upper and lower support plates 108, 117 include features or coatings (not shown) that enhance the fixation of the intervertebral implant 100 in some embodiments. For example, the engagement surfaces 112, 119 are roughened such as by chemical etching, bead-blasting, sanding, grinding, serrating, and/or diamond-cutting in some instances. All or a portion of the engagement surfaces 112, 119 can also be coated with a biocompatible and osteoconductive material such as hydroxyapatite (HA), tricalcium phosphate (TCP), and/or calcium carbonate to promote bone in growth and fixation. Alternatively, osteoinductive coatings, such as proteins from transforming growth factor (TGF) beta superfamily, or bone-morphogenic proteins, such as BMP2 or BMP7, can be used. Moreover, the engagement structures 113, 122 comprise spikes, ridges, keels, fins, posts, or other bone engaging protrusions for initial fixation of the intervertebral implant 100 and/or to prevent migration in the lateral or anterior/posterior directions in some instances. In some instances, the engagement surfaces 112, 119 include serrations, diamond cuts, and/or other surface textures.

The upper support plate 108 has a thickness 114 between the articulating surface 109 and the opposing engagement surface 112. In some embodiments, the thickness 114 of the upper support plate 108 is sufficient to allow one or more magnetic components of the intervertebral implant to be positioned therein. In some instances, the thickness 114 is between about 2 mm and about 25 mm, and in some instances between about 5 mm and about 15 mm. Similarly, the lower support plate 117 has a thickness 120 between the articulating surface 118 and the opposing engagement surface 119. In some embodiments, the thickness 120 of the lower support plate 117 is sufficient to allow one or more magnetic components of the intervertebral implant to be positioned therein. In some instances, the thickness 120 is between about 2 mm and about 25 mm, and in some instances between about 5 mm and about 15 mm.

The intervertebral implant 100 and, in particular, the articulating portion 107 provides relative pivotal, rotational, and/or translational movement between the adjacent vertebrae 14, 16 to maintain or restore motion substantially similar to the normal bio-mechanical motion provided by a natural intervertebral disc. In some embodiments the articulating portion 107 comprises a ball-and-socket joint formed by the upper and lower portions 102, 103. In one such embodiment, shown in FIG. 4, the articulating surface 109 of the upper portion 102 includes a recess 123, shown in phantom, adapted to pivotally mate with a projection 127 extending from the articulating surface 118 of the lower portion 103. Together the recess 123 and the projection 127 form the ball-and-socket joint of the articulating portion 107. In this manner, the upper and lower portions 102, 103 are configured to permit pivotal motion about a number of axes, including lateral or side-to-side pivotal movement about longitudinal axis L, anterior-posterior pivotal movement about a transverse axis T, rotational pivotal movement about a rotational axis R, and combinations thereof. In some embodiments, the recess 123 is shaped (e.g. with a larger radius of curvature than the projection 127) to allow translational movement along the longitudinal axis L, the transverse axis T, and/or combinations thereof.

The support plate 108 includes the articulating surface 109. Referring more specifically to FIG. 4, the articulating surface 109 includes the recess 123 as described above. In the current embodiment, the recess 123 is substantially shaped as a spherical socket. However, it should be understood that in other configurations the recess 123 has other shapes, such as, for example, cylindrical, elliptical, other arcuate configurations, and/or non-arcuate configurations. The recess 123 is shaped to mate with the projection 127 of the lower portion 103 to provide at least some motion to the intervertebral implant 100. The remaining portion of the articulating surface 109 is contoured to further facilitate the motion-preserving features of the intervertebral implant 100 in some embodiments. For example, in the current embodiment the remaining portions of the articulating surface 109 are shaped for interfacing with bladders of articulating portion 107, as described in greater detail below. In some instances, the remaining portions of the articulating surface 109 are angled or sloped as they extend from the edge of the recess 123 to the edges of the articulating surface 109 to allow for a greater range of motion than would be possible if the remaining portion of the articulating surface was planar. In other embodiments, the remaining portions of the articulating surface 109 substantially planar, include stop portions, are angled in one direction but not another direction, and/or are otherwise configured to facilitate motion-preserving features, the insertion, and/or the general use of the intervertebral implant 100.

Further, although the recess 123 is illustrated as having a generally smooth, uninterrupted surface, it should be understood that a surface depression, cavity, or groove can be defined along a portion of the recess to aid in clearing out matter, such as particulate debris, that may be disposed between the abutting articulating surfaces 109, 118 of upper and lower portions 102, 103. In one such embodiment, the surface of the projection 127 defines a generally smooth, uninterrupted articular surface. In another embodiment, each of the recess 123 and the convex projection 127 includes a surface depression or recess facilitate removal of particulate matter disposed between the abutting articulating surfaces 109, 118.

Referring to FIGS. 3-8, the support plate 108 also includes engagement surface 112 with the engagement structure 113 extending therefrom. In the current embodiment, the engagement structure 113 comprises a single flange member or keel that extends substantially across the engagement surface 112 in a direction substantially transverse to the longitudinal axis L. The engagement structure 113 is sized and shaped for disposition within a preformed opening in the adjacent vertebra 14. As best seen in FIGS. 6 and 8, the engagement structure 113 includes opposing surfaces 128 and 129 separated by a width 132. In the current embodiment, the surfaces 128 and 129 are substantially planar and the width 132 is substantially constant along the length and height of the engagement structure 113. However, in other embodiments the width 132 varies along the length and/or height of the engagement structure 113. For example, in some embodiments the width 132 is narrowed towards at least one end and/or the upper portion of the engagement structure 113 compared to the other portions of the structure. In some embodiments, the width 132 is narrowed such that the engagement structure 113 is capable of cutting into the bone structure to facilitate engagement of the intervertebral implant 100 with the adjacent vertebra 14, 16. Further, in some embodiments the engagement structure 113 is sharp enough that it is capable of being inserted without a preformed opening in the adjacent vertebra 14. In some embodiments, the width 132 varies such that the surfaces 128 and 129 are non-planar. In general the width 132 of the engagement structure 113 is within a range of 0.5 mm to 10 mm, but can be smaller or greater in some embodiments.

The engagement structure 113 also includes a pair of openings 133 extending therethrough between the opposing surfaces 128, 129 to facilitate bone in-growth to enhance fixation to the adjacent vertebra 14. However, it should be understood that any number of openings can be defined through the engagement structure 113, including a single opening or three or more openings. It should also be understood that the openings 133 need not necessarily extend entirely through the engagement structure 113, but can alternatively extend partially therethrough. It should further be understood that the engagement structure 113 need not necessarily define any openings extending either partially or entirely therethrough. Additionally, although the openings 133 are illustrated as having a circular configuration, it should be understood that other shapes, sizes, and configurations of the openings are also contemplated.

In the current embodiment, the engagement structure 113 is substantially perpendicular to the engagement surface 112. In particular, as better seen in FIG. 6, in the current embodiment the surface 128 extends from the engagement surface 112 at an angle 137, which is approximately 90°, and the surface 129 extends from the engagement surface 112 at an angle 138, which is approximately 90°. Thus, as shown the surfaces 128 and 129 are substantially parallel to one another and the engagement structure 113 generally extends from the engagement surface 112 at approximately a 90° angle. In other embodiments, each of the angles 137 and 138 have other values within the range of 10° to 170° such that the surfaces 128 and 129 are substantially parallel. In yet other embodiments, each of the angles 137 and 138 have values within the range of 10° and 170°, but such that the surfaces 128 and 129 are not substantially parallel. The precise choice of angles 137, 138 can be adapted for the particular patient and/or application. In the current embodiment, the engagement structure 113 as a whole is approximately centrally located along the transverse axis T of the intervertebral implant 100. However, it should be understood that the engagement structure 113 is located in other positions and orientations in other embodiments, including orientations substantially along the longitudinal axis L and oblique angles between the longitudinal and transverse axes L, T.

The portions of engagement surface 112 and engagement structure 113 that are in direct contact with vertebral bone are coated with a bone-growth promoting substance in some embodiments. For example, in one aspect the engagement surface 112 and the engagement structure 113 are coated with a bone-growth promoting substance to promote bony engagement with the adjacent vertebra. Further, in some embodiments the openings 133 can be filled with a bone-growth promoting substance to further enhance bone in-growth. Also, the engagement surface 112 and engagement structure 113 can be roughened in lieu of or prior to application of the bone-growth promoting surface.

Referring more specifically to FIG. 7, shown is a diagrammatic top view of the upper portion 102 of the intervertebral implant 100. As shown, the upper portion 102 includes a recess 153. The recess 153 has a horseshoe shape with a substantially uniform width 157. However, in alternative embodiments the width 157 of the recess 153 varies along the length of the recess 153. Moreover, as shown in the illustrated embodiment, the recess 153 is approximately centered about the midpoint between a lateral end of the support plate 108 and the point at the engagement surface 112 where the engagement structure 113 makes contact. In some instances, the recess 153 is positioned closer to the edge of the support plate 108. In other instances, the recess 153 is positioned closer to the center of the support plate 108.

Further, the recess 153 has a left lateral portion 154 positioned on the engagement surface 128 side of the engagement structure 113, a right lateral portion 155 positioned opposite the left lateral portion 154 on the surface 129 side of the engagement structure 113, and an anterior portion 156 extending between and connection the left and right lateral portions 154, 155. In some embodiments, the portions 154, 155, 156 of the recess 153 are discrete, separate recesses.

Referring to FIG. 8, shown is a diagrammatic cross section view of the upper portion 102 of the intervertebral implant 100. The cross section view of FIG. 8 is taken along section line 8-8 shown in FIG. 7. As better seen in FIG. 8, the recess 153 extends from the engagement surface 112 into the support plate 108 and has a generally uniform depth 158. The depth 158 of the recess 153 is approximately half the thickness 114 of the upper portion 102 in the illustrated embodiment. In alternative embodiments, the depth 158 is non-uniform and varies along the length of the recess 153. In some instances, the depth 158 is between about 1 mm and about 12.5 mm, and in some instances between about 2.5 mm and about 7.5 mm. In any case, the depth 158 of the recess 153 is sufficient to allow one or more permanent magnets 159, 160, 161 to be positioned therein. For example, referring back to FIG. 7, in the current embodiment, there are three permanent magnets 159-161 positioned within the recess 153. The spacing between the permanent magnets 159-161 is substantially uniform in the illustrated embodiment. However, in some embodiments the spacing between the permanent magnets 159-161 is not uniform. In the current embodiment, the permanent magnets 159-161 are generally cylindrical in shape. For example, the diameter of the cylindrically shaped permanent magnets 159-161 is approximately equivalent to or slightly less than the width 157 of the recess 153, and therefore allows translation of the magnets 159-161 along the recess 153. Moreover, in the current embodiment, the lengths of the cylindrically shaped permanent magnets 159-161 are substantially similar and substantially equivalent to the depth 158 of the recess 153. In the illustrated embodiment, the upper surface of the magnets 159-161 is coplanar with the top surface of the recess 153 and the engagement surface 112, and the lower surface of the magnets 159-161 is coplanar with the bottom of the recess 153. In some instances, the lengths of the cylindrical shaped permanent magnets 159-161 vary. Also, in some instances, the lengths of the cylindrical shaped permanent magnets 159-161 are less than the depth 158 of the recess 153. In alternative embodiments, the shape of the magnets 159-161 are different. For example, the magnets 159-161 have a spherical, elliptical, cubic, and/or other configurations in some instances. In some instances, one or more of the magnets 159-161 include electronic or electro-magnets.

In some instances the magnets 159-161 are sized to fit snugly within the recess 153. In that regard, the diameter of the magnets 159-161 is substantially the same as the width 157 of the recess. In other instances, the recess 153 includes a lip (not shown) that extends around the perimeter of the recess 153 adjacent the engagement surface 112. In some instances, an upper surface of the lip is coplanar with the engagement surface 112. In that regard, the lip reduces the width of the portion of the recess 153 that is coplanar to the engagement surface 112. In other words, the width 157 of the recess 153 is uniform from the bottom of the recess 153 extending upward to the lip. At the lip, the width of the recess 153 is slightly less. In some instances the diameter of the magnets 159-161 are sized substantially similar to the width 157 of the recess 153. In this respect, the lip prevents the magnets 159-161 from coming free from the recess 153. In other instances, the diameter of the magnets 159-161 is slightly less than the width 157 of the recess 153, but slightly greater than the width of the lip portion of the recess that is coplanar with the engagement surface. Said another way, in some instances, the diameter of the magnets 159-161 is slightly less than the width 157 of the recess 153, but slightly greater than the spacing between the lips of the recess 153. In that regard, the recess 153 accommodates adjustment of the magnets 159-161 in a direction along the path of the recess 153 and coplanar to the engagement surface 112 while preventing the magnets 159-161 from becoming free of the recess 153. In an alternative embodiment, the magnets 159-161 are disposed in an opening or bore disposed in the support plate 108. In that regard, the magnets 159-161 are disposed below the engagement surface 112 and above the articulating surface 109. In some instances, the bore or opening is shaped and sized in a manner similar to the shape and size of the recess 153.

As discussed above, in some embodiments, the portions 154, 155, 156 of the recess 153 are discrete, separate recesses. In that regard, in some instances, the range of movement of the magnets 159-161 is limited by the discrete, separate recesses 154, 155, 156. For example, in some instances, the range of movement of the magnet 159 is limited to the boundary of the right lateral portion 154, the range of movement of the magnet 160 is limited to the boundary of the anterior portion 155, and the range of movement of the magnet 161 is limited to the boundary of the left lateral portion 156.

The support plate 117 of the lower portion 103 includes the articulating surface 118, as discussed above. Moreover, the articulating surface 118 includes the projection 127 having a convex shape. As better shown in FIG. 10, the projection 127 is configured as a portion of a spherical-shaped ball in some embodiments. It should be understood that other configurations of the projection 127 are utilized in other embodiments, such as, for example, cylindrical, elliptical or other arcuate configurations or possibly non-arcuate configurations. The remaining portion of the articulating surface 118 is substantially planar in the current embodiment. However, it should be understood that the remaining portion of articulating surface 118 is non-planar or has non-planar/planar combination configurations in other embodiments. For example, in some embodiments the articulating surface 118 includes an angular or conical configuration extending about the projection 127. Further, in some embodiments the surface of the projection 127 is interrupted by a surface depression, cavity, groove, or other interruption extending along the projection. The interruption facilitates the removal of matter disposed between abutting portions of the upper and lower portions 102, 103 forming the articulating portion 107. More specifically, the interruption aids in clearing out matter such as, for example, particulate material, that is disposed between the abutting articulating surfaces 109, 118 of the upper and lower portions 102, 103.

Now referring to FIGS. 9-11, the lower support plate 117 also includes the engagement surface 119 with the engagement structure 122 extending therefrom. In the current embodiment, the engagement structure 122 is substantially similar to the engagement structure 113 of the upper portion 102. The engagement structure 122 comprises a single flange member or keel that extends substantially across the engagement surface 119 in a direction substantially transverse to the longitudinal axis L, as better seen in FIG. 3. The engagement structure 122 is sized and shaped for disposition within a preformed opening in the adjacent vertebra 16. The engagement structure 122 includes opposing surfaces 139 and 142 separated by a width 143, as best seen in FIG. 10. In the current embodiment, the surfaces 139 and 142 are substantially planar and the width 143 is substantially constant along the length and height of the engagement structure 122 and is substantially equal to the width 132 of the engagement structure 113 of the upper portion 102. However, in other embodiments the width 143 varies along the length and/or height of the engagement structure 122. For example, in some embodiments the width 143 is narrowed towards at least one end and/or the upper portion of the engagement structure 122 compared to the other portions of the structure. In some embodiments, the width 143 is narrowed such that the engagement structure 122 is capable of cutting into the bone structure to further facilitate engagement of the intervertebral implant 100 with the adjacent vertebra 16. Further, in some embodiments the engagement structure 122 is sharp enough that it is capable of being inserted without a preformed opening in the adjacent vertebra 16. In some embodiments, the width 143 varies such that the surfaces 139 and 142 are non-planar. Also, the width 143 of the engagement structure 122 is different from the width 132 of the engagement structure 113 in some embodiments. In general, the width 143 of the engagement structure 122 is within a range of 0.5 mm to 10 mm, but can be smaller or greater in some embodiments.

As best seen in FIGS. 3 and 4, the engagement structure 122 also includes a pair of openings 147 extending therethrough between the opposing surfaces 139, 142 to facilitate bone in-growth to enhance fixation to the adjacent vertebra 16. However, it should be understood that any number of openings can be defined through the engagement structure 122, including a single opening or three or more openings. It should also be understood that the openings 147 need not necessarily extend entirely through the engagement structure 122, but can alternatively extend partially therethrough. It should further be understood that the engagement structure 122 need not necessarily define any openings extending either partially or entirely therethrough. Additionally, although the openings 147 are illustrated as having a circular configuration, it should be understood that other shapes, sizes, and configurations of the openings are also contemplated.

In the current embodiment, the engagement structure 122 is substantially perpendicular to the engagement surface 119. In particular, in the current embodiment the surface 139 extends from the engagement surface 119 at an angle 149, which is approximately 90°, and the surface 62 extends from the engagement surface at an angle 70, which is approximately 45°. Thus, as shown the surfaces 139 and 142 are substantially parallel to one another and the engagement structure 122 generally extends from the engagement surface 119 at approximately a 90° angle. In other embodiments, each of the angles 148 and 149 have other values within the range of 10° to 170° such that the surfaces 139 and 142 are substantially parallel. In yet other embodiments, each of the angles 148 and 149 have values within the range of 10° and 170°, but such that the surfaces 139 and 142 are not substantially parallel. The precise choice of angles 148, 149 can be adapted for the particular patient and/or application. Further, the angles 148, 149 can be selected for a particular orientation of the engagement structure 122 with respect to the engagement structure 113.

As shown in FIG. 4, when the intervertebral implant 100 is in a neutral position the engagement structure 122 extends in a direction substantially parallel to the engagement structure 113 of the upper portion 102. In other embodiments, the engagement structure 122 is at an angle with respect to the engagement structure 113 when the intervertebral implant 100 is in a neutral position. In some embodiments, the engagement structure 122 is substantially perpendicular to the engagement structure 113. In yet other embodiments, the engagement structure 122 is substantially aligned with the engagement structure 113.

In the current embodiment, the engagement structure 122 as a whole is approximately centrally located along the longitudinal axis L of the intervertebral implant 100. However, it should be understood that the engagement structure 122 is located in other positions and orientations in other embodiments, including off-center locations. In some embodiments the engagement structure 122 is offset from the engagement structure 113 of the upper portion 102 along the longitudinal axis L and/or the transverse axis T of the intervertebral implant 100.

The portions of engagement surface 119 and engagement structure 122 that are in direct contact with vertebral bone are coated with a bone-growth promoting substance in some embodiments. For example, in one aspect the engagement surface 119 and the engagement structure 122 are coated with a bone-growth promoting substance to promote bony engagement with the adjacent vertebra 16. Further, in some embodiments the openings 133 can be filled with a bone-growth promoting substance to further enhance bone in-growth. Also, the engagement surface 119 and engagement structure 122 can be roughened in lieu of or prior to application of the bone-growth promoting surface.

Referring again to FIGS. 2-11, in some embodiments the intervertebral implant 100 includes one or more notches 152 in the upper and/or lower portions 102, 103, or other types of structure, for receiving and engaging with a corresponding portion of a surgical instrument (not shown) to aid in the manipulation and insertion of the intervertebral implant 100 within the intervertebral space between the adjacent vertebrae. The surgical instrument (not shown) is preferably configured to hold the upper and lower portions 102, 103 at a predetermined orientation and spatial relationship relative to one another during the manipulation and insertion of the intervertebral implant 100, and to release the upper and lower portions 102, 103 once properly positioned between the adjacent vertebrae.

Referring back to FIGS. 3 and 4, the articulating portion 107 of the intervertebral implant 100 includes a multi-bladder support 162 between the upper support plate 108 and the lower support plate 117. More specifically, the multi-chamber support 162 comprises a plurality of interconnected bladders 163, 164, 165, 166 that are disposed between the articulating surfaces 109 and 118. In some instances, the multi-chamber support 162 is formed of a flexible polymer material. In alternative embodiments the bladders 163-166 of the multi-chamber support 162 comprises a silicon, urethane, or other biocompatible flexible material. In some instances, the bladders comprise a woven mesh. The illustrated multi-chamber support 162 includes four bladders 163-166 that are connected by three orifices 172, 173, 174. In general, the orifices 172-174 in between the bladders 163-166 mechanically restrict the flow of a fluid between the bladders 163-166 due to their reduced diameter and size relative to the bladders 163-166 themselves. In that regard, the orifices 172-174 amplify the effect of changing the viscosity of the fluid disposed therein, thus providing increased or decreased damping depending on the strength of the magnetic field at the orifices 172-174. In some instances, the intervertebral implant 100 includes additional mechanical support. In that regard, some embodiments of the intervertebral implant include a peripheral band and/or a vertical post.

Referring to FIGS. 3 and 4, and FIGS. 9-11, the bladders 163-166 are described in greater detail. In the current embodiment, there are four total bladders 163-166. In some instances, there are a greater number of bladders, or a lesser number of bladders. In the current embodiment, the bladders 163-166 are fixedly attached to the articulating surface 118 of the lower support plate 117. In alternative embodiments, the bladders 163-166 are fixedly attached to the articulating surface 109 of the upper support plate 108. In other instances, the bladders 163-166 are fixedly attached to both articulating surfaces 109, 118 of the respective upper and lower support plates 108, 117. In yet another instance, the bladders 163-166 are disposed between the upper and lower support plates 108, 117 with an outer sheath that contains the bladders 163-166 between the upper and lower support plates 108, 117 and within an area defined by the anterior, posterior, and lateral edges of the upper and lower support plates 108, 117.

In some instances, the multi-chamber support 162 controls the amount of cushioning or support provided by the intervertebral implant 100 and/or the amount of motion allowed by the intervertebral implant 100. In some instances, the multi-chamber support 162 allows the intervertebral implant 100 to compress or elastically deform under compressive loads. Further, in some instances the multi-chamber support 162 allows the intervertebral implant 100 to expand or elastically stretch in response to a force that pulls the upper and lower support plates 108 and 117 away from one another. Further, in some instances, the multi-chamber support 162 allows both compression and expansion of the intervertebral implant 100. In some instances, a portion of the intervertebral implant 100 is compressed while another portion of the intervertebral implant 100 is expanded. For example, when positioned in the cervical spine, compression of the posterior portion of the intervertebral implant 100 compresses the bladders 163, 166. Likewise, compression of the anterior portion of the intervertebral implant 100 compresses the bladders 164, 165. As another example, in a lateral bending to the patient's right side, the lateral right side of the intervertebral implant 100 compresses, thereby compressing the bladders 163, 164. Likewise, in a lateral bending to the patient's left side, the lateral left side of the intervertebral implant 100 compresses, thereby compressing the bladders 165, 166.

In some embodiments of the present disclosure, the multi-chamber support 162 adjusts the amount of the support and/or motion of the intervertebral implant 100 based on parameters associated with the patient's physical activity. For example, in some instances the multi-chamber support 162 adjusts based on an anatomical load imparted on the implant. In other embodiments, the adjustment is based on acceleration, motion, pressure, and/or other parameters associated with the vertebral joint 12. In some instances, the stiffness of the multi-chamber support 162 is adjusted in order to adjust the support provided by the intervertebral implant 100 and/or the motion allowed by the intervertebral implant 100. In that regard, the stiffness of the multi-chamber support 162 is adjusted in a different manner depending on the type of support utilized. In some instances the intervertebral implant 100 includes all of the same type of supports. In other instances, the intervertebral implant 100 includes at least two different types of support in accordance with the present disclosure. In some instances, the implant combines one or more of the supports of the present disclosure with previously known implant features and/or supports. In some instances, the multi-chamber support 162 continually adjusts the amount of support and/or cushioning of the intervertebral implant 100. In that regard, in some instances, the intervertebral implant 100 includes electronic controls to control the continual adjustment provided by the multi-chambers support 162. In some instances, the intervertebral implant 100 includes a controller, battery, antenna, and/or accelerometer to control the intervertebral implant 100 and/or acquire data.

Referring to FIGS. 3 and 4, the bladders 163-166 are shown with the intervertebral implant 100 in a neutral position. As shown, the bladders 163-166 are shaped in a manner substantially similar to one another when the implant is in the neutral position. For example, referring to FIGS. 4 and 10, each of the bladders 163-166 has a respective height 168, 169, 170, 171. Each one of the heights 168-171 is defined by the distance between the upper and lower surfaces of the respective bladders 163-166. In the current embodiment, the heights 168-171 of the respective bladders 163-166 are substantially similar to one another in the neutral position of the intervertebral implant 100. In that regard, the heights 168-171 of the bladders 163-166 are approximately equivalent to twice the thickness of either the upper support plate 108 or the lower support plate 117. In some instances, the bladders 163-166 have heights 168-171 between about 4 mm and about 50 mm, and in some instances between about 10 mm and about 15 mm. In alternative embodiments, each height 168-171 of the bladders 163-166 is approximately equivalent to the thickness 120 of the lower support plate 117. In some instances each of the heights 168-171 of the bladders 163-166 is greater than the thickness 120 of the lower support plate 117, and in some instances each of the heights 168-171 of the bladders 163-166 is less than the thickness 120 of the lower support plate 117. In the current embodiment, the surfaces of the bladders 163-166 that contact the upper and lower support plates 108, 117 are substantially planar and parallel to one another. In some instances, the surfaces of the bladders 163-166 that contact the upper and lower support plates 108, 117 are non-planar and/or arcuate surfaces. In alternative embodiments, the surface of one or more of the bladders 163-166 that contacts the upper support plate 108 is substantially planar, but does not extend parallel to the surface of the bladders 163-166 that contacts the lower support plate 117. In some instances, each height 168-171 of the bladders 163-166 is between about 2 mm and about 25 mm, and in some instances between about 5 mm and about 15 mm. In alternative embodiments, one or more of the heights 168-171 are different. In some instances, one or more of the bladders 163-166 limit another one or more of the bladders 163-166 from contacting the articulating surface 109 when the intervertebral implant 100 is in a neutral position. In that regard, one or more of the bladders 163-166 make contact with the articulating surface 109 only the intervertebral implant 100 is in a non-neutral articulation position.

As better seen in FIG. 11, the bladders 163-166 each have respective lengths 193, 194, 195, 196 and widths 203, 204, 205, 206. In the current embodiment, the lengths 193-196 of the bladders 163-166 are substantially uniform and approximately equivalent in the neutral position of the intervertebral implant 100. For example, each of the lengths 193-196 of the respective bladders 163-166 is about one third the length of the lower support plate 117 along the longitudinal axis L. In the current embodiment, the widths 203-206 of the bladders 163-166 are substantially uniform and approximately equivalent in the neutral position of the intervertebral implant 100. For example, each of the widths 203-206 of the respective bladders 163-166 is approximately half the length L of the bladders 163-166. In other instances, each of the lengths 193-196 of the bladders 163-166 vary in size. Also, in some instances, each of the widths 203-206 of the bladders 163-166 vary in size. In other words, in alternative embodiments, the lengths 193-196 and the widths 203-206 of the respective bladders 163-166 are different. In some instances, each of the lengths 193-196 of the bladders 163-166 is between about 4 mm and about 50 mm, and in some instances between about 10 mm and about 30 mm. In some instances, each of the widths 203-206 of the bladders 163-166 is between about 2 mm and about 25 mm, and in some instances between about 5 mm and about 15 mm. Referring to FIG. 9, a perspective view of the lower portion 103 shows the respective lengths 193-196 and widths 203-206 of the bladders 163-166 relative to the respective heights 168-171.

As better seen in FIGS. 9 and 11, the bladders 163-166 are arranged in a horseshoe like fashion around the convex projection 127 and inside the front and lateral edges of the articulating surface 118. Each of the bladders 163-166 are connected in sequence by orifices 172-174. More specifically, the bladders 163, 164 are connected by orifice 172, the bladders 164, 165 are connected by orifice 173, and the bladders 165, 166 are connected by orifice 174.

Referring again to FIG. 11, in the present embodiment, the bladders 163-166 are equally spaced about the outer portion of the intervertebral implant 100. In particular, the bladders 163, 164 are positioned on one lateral side of the intervertebral implant 100, while the bladders 165, 166 are positioned on the other lateral side of the intervertebral implant 100, and substantially symmetrical with the bladders 162, 164 relative to a midline of the intervertebral implant 100 extending in an anterior-posterior direction.

As illustrated in FIGS. 12-15, the bladders 163-166 have a biocompatible fluid 140 for load bearing and motion attenuation. For example, the biocompatible fluid can include water, saline, PEG, glycerol, plasma extender, and hydrocarbon solvents. In some instances, magnetically sensitive particles are added to modify the rheological behavior of the biocompatible fluid. In some instances, the rheological behavior of the biocompatible fluid allows for variations in the stiffness and damping of the multi-chamber support 162. In other instances, magnetically sensitive particles are added to the biocompatible fluid to modify the rheological behavior of the fluid. In alternative embodiments, a ferrofluid or electrorheological fluid is disposed within the multi-chamber support 162.

In one particular embodiment, the fluid 140 includes a magnetorheological fluid. In that regard, the magnetorheological fluid 140 has variable viscosity. In one instance, the viscosity of the magnetorheological fluid 140 varies based on the strength of a magnetic field applied to the magnetorheological fluid 140. The greater the magnetic field applied to the magnetorheological fluid 140, the greater the viscosity of the fluid. In some instances, the magnetorheological fluid 140 comprises a plurality of ferrous particles suspended in a carrier fluid 144. In some instances, the carrier fluid is a silicon based fluid and the ferrous particles are iron particulate. Under the presence of a magnetic field the ferrous particles are polarized and form a chain-like formation within the carrier fluid. Generally the ferrous particles form along the direction of the magnetic flux passing through the magnetorheological fluid 140, such that the strength of the ferrous particle chain is directly related to the strength of the magnetic field.

Together, the bladders 163-166 and magnetorheological fluid 140 therein act as a shock absorber for the intervertebral implant 100. By adjusting the viscosity of magnetorheological fluid 140 the stiffness and damping of the bladders 163-166, and in turn the intervertebral implant 100, is adjusted Referring generally to FIGS. 12-14, an exemplary embodiment of a pair of chambers 400, 402 is shown. The pair of chambers 400, 402 is used as two or more of the bladders 163-166 of the intervertebral implant 100 in some instances. FIG. 12 is a diagrammatic front view of two exemplary chambers 400, 402 of a multi-chamber support of the intervertebral implant shown in FIGS. 2-4 illustrated in a neutral position. FIG. 13 is another diagrammatic front view of two exemplary chambers 400, 402 of the multi-chamber support of the intervertebral implant similar to that of FIG. 12, but showing the chambers in a first articulation position. FIG. 14 is another diagrammatic front view of two exemplary chambers 400, 402 of the multi-chamber support of the intervertebral implant similar to that of FIGS. 12 and 13, but showing the chambers in a second articulation position. In some instances the exemplary chambers 400, 402 shown in FIGS. 12-14 have an inner lining 404 that contains magnetorheological fluid 140. Moreover, similar to the bladders 164, 165, the exemplary bladders shown in FIGS. 12-14 are connected by an orifice 406.

FIG. 12 illustrates a diagrammatic front view of two exemplary chambers 400, 402 that are substantially the same as the bladders 163-166 of the intervertebral implant 100 in the neutral position of FIG. 4. That is, when the intervertebral implant 100 is in the neutral position, the dimensions of each of the chambers 400, 402 are substantially equivalent to the dimensions of each of the bladders 163-166. However, as the upper portion 102 compresses down on the chambers 400, 402 the shape and dimensions of the chambers 400, 402 change. For example, illustrated in FIG. 13 is another diagrammatic front view of the same two exemplary chambers 400, 402 shown in FIG. 12, but shown with the chamber 400 under compression. In that instance, the magnetorheological fluid 140 residing in the chamber 400 passes through the orifice 406 and into the chamber 402. In some instances, the change in the volume of the chamber 400 can be marginally reduced, and in some instances the change in volume of the chamber 400 can be substantial. In any case, the magnetorheological fluid 140 that resides in the chamber 400 is displaced into the chamber 402 such that the chamber 402 increases in an amount substantially equivalent to the decrease in volume of chamber 400. Referring to FIG. 14, illustrated is another diagrammatic front view of the same two exemplary chambers 400, 402 of the intervertebral implant 100, but shown with the chamber 402 under compression. That is, as shown in FIG. 14, the chamber 400 is compressed between the articulating surfaces 109, 118. In contrast to the discussion with respect to FIG. 13, in this instance, the magnetorheological fluid 140 in the chamber 402 is displaced into the chamber 400. In particular, the reduction in the volume of the magnetorheological fluid 140 maintained in the chamber 400 is substantially equivalent to the increase in volume of the magnetorheological fluid 140 that is displaced through the orifice 406, into the chamber 400.

Referring to FIG. 15, illustrated is a diagrammatic front view of a multi-chamber support 420, according to an alternative embodiment of the present disclosure. The multi-chamber support 420 has two chambers 422, 424. In some instances, the chambers 422, 424 are comprised of the same material as the chambers 400, 402 shown in FIGS. 12-14 and the bladders 163-166. The dimensions of the chambers 422, 424 are substantially equivalent to the dimensions of the bladders 163-166. The chambers 422, 424 are connected by an orifice 426, similar to each of the orifices 172-174 discussed above. Moreover, an end of the chamber 422 is connected to a reservoir 428 by an orifice 430. Likewise, an end of the chamber 424 is connected to a reservoir 432 by an orifice 434. Each of the reservoirs 428, 432 is reduced in size relative to the chambers 422, 424 in the neutral position of the intervertebral implant 100. In some instances, the reservoirs 428, 432 are comprised of the same material as the chambers 422, 424. In the illustrated embodiment, the multi-chamber support 420 contains a biocompatible fluid 426, similar to the fluid that is contained in the chambers 400, 402 shown in FIGS. 12-14 and the bladders 163-166 of the intervertebral implant 100. More specifically, the chambers 422, 424 and the reservoirs 428, 432 contain the biocompatible fluid 436. In the illustrated embodiment, the biocompatible fluid includes a magnetorheological fluid, substantially similar to the magnetorheological fluid 140, discussed above, and having the substantially similar qualities and properties thereof.

In some instances, the reservoirs 428, 432 include magnetorheological fluid 436 while the intervertebral implant 100 is in the neutral position shown in FIG. 4. In other instances, the reservoirs 428, 432 are substantially free of magnetorheological fluid when the intervertebral implant 100 is in the neutral position shown in FIG. 4. In yet other instances, one of the reservoirs 428, 432 contains more magnetorheological fluid 436 than the other of the reservoirs 428, 432 while the intervertebral implant 100 is in the neutral position. In yet other instances, the amount of magnetorheological fluid 140 contained in the reservoirs 428, 432 is substantially equivalent while the intervertebral implant 100 is in the neutral position shown in FIG. 4. In other embodiments, each of the reservoirs 428, 432 contain different amounts of magnetorheological fluid 436 while the intervertebral implant 100 is in the neutral position shown in FIG. 4. The exemplary chambers 422, 424 shown in FIG. 15 function similarly to the exemplary chambers 400, 402 shown in FIGS. 12-14 in many aspects, however, in response to the upper portion 102 compressing down on the exemplary chambers 422, 424, the magnetorheological fluid 436 is able to pass into and/or out of the reservoirs. For example, in response to the upper portion 102 compressing the chamber 422, the magnetorheological fluid 436 is able to pass through the orifice 426 into the chamber 424, and in some instances, also through the orifice 434 into the reservoir 432. In some instances the exemplary chambers 422, 424 and the reservoirs 428, 432 shown in FIG. 15 have an inner lining 4425 that contains magnetorheological fluid 140.

Although the intervertebral implant 100 and the articulating portion 107 have been illustrated and described as providing a specific combination of articulating motion, it should be understood that other combinations of articulating movement are also possible and are contemplated as falling within the scope of the present disclosure. In addition, the articulating motion is biased towards a particular direction and/or limited in a particular direction in some instances. Further, the intervertebral implant 100 can include stops to totally prevent motion in a certain direction past a predetermined threshold.

Further, in some embodiments the articulating portion 107 is a completely separate portion of the intervertebral implant 100. That is, the articulating portion 107 is not formed by portions of the upper and lower portions 102, 103, but rather is connected to, mated with, or otherwise oriented with the upper and lower portions to provide at least some motion to the intervertebral implant 100. In one such embodiment, the articulating portion 107 is formed of a resilient, elastic material.

Figure 16:
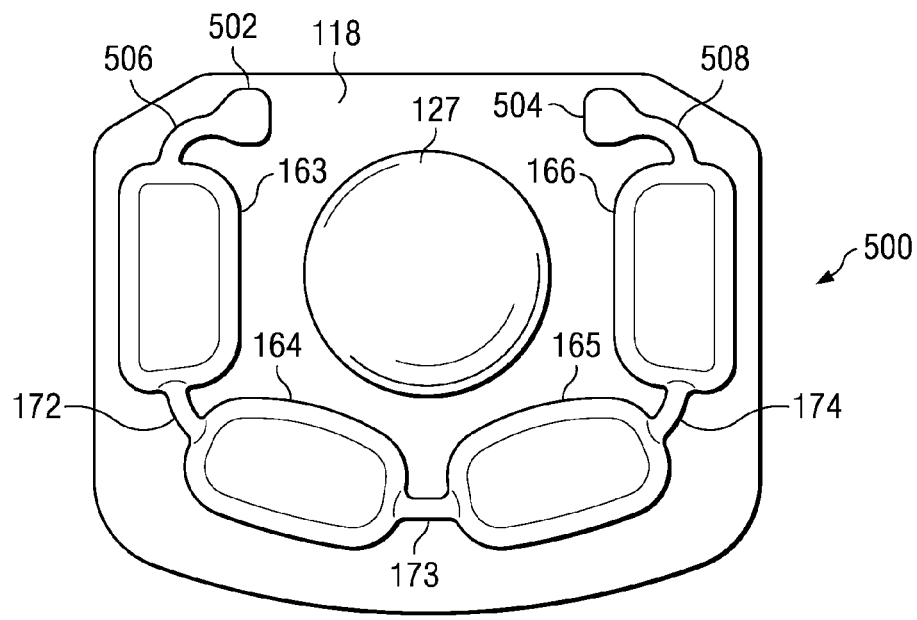
FIG. 16 is a diagrammatic top view of a lower portion of an intervertebral implant according to an alternative embodiment of the present disclosure.

Referring to FIG. 16, shown is a lower support plate 500 of an intervertebral implant according to an alternative embodiment of the intervertebral implant 100. The lower support plate 500 is similar to the lower support plate 117 shown in FIGS. 9 and 11. Identical or equivalent elements are identified by the same reference numerals, and the following discussion focuses primarily on the differences. In particular, the lower support plate 500 includes reservoirs 502, 504 that are respectively connected to the bladders 163, 166. In that regard, the reservoir 502 is connected to the bladder 163 at the orifice 506. Also, the reservoir 504 is connected to the bladders 166 at the orifice 508.

Referring to FIGS. 3, 5, and 7, a more detailed description of the function of the permanent magnets 159-161 is now provided. The magnets 159-161 are disposed in the recess 153. In the current embodiment, the positions of the magnets 159-161 are adjustable along the path of the recess. For example, the magnets 159-161 are adjustable for translational movement along the path defined by the recess 153. In some embodiments, the permanent magnets 159-161 are configured in a manner so that the spacing between each of the permanent magnets 159-161 remains constant during adjustment. For example, in some instances the magnets 159-161 are disposed in a horseshoe shaped plate in a manner so that the positions of the magnets 159-161 are fixed with respect to one another. In that regard, in some instances, the horseshoe shaped plate is sized so that it can translate along the path defined by the recess 153. In that instance, the translation of the horseshoe shaped plate results in translation of the magnets 159-161 along a path defined by the recess 153. In that regard, the horseshoe shaped plate includes a screw mechanism that is used to adjust the position of the horseshoe shaped plate and/or one or more of the magnets 159-161. In that regard, the adjusting screw mechanism is accessible before, during, and/or after surgery. In some instances, the adjusting screw mechanism is easily accessible after implantation through a needle incision and a minimally invasive method. In other instances, the adjusting screw mechanism is easily accessible after implantation to allow minimally evasive percutaneous method. In other embodiments, spacers are disposed in the recess 153 to separate the magnets 159-161. In that regard, the distance between each of the magnets 159-161 is adjustable. For example, different sized spacers are used to create various positions of the magnets 149-161 in the recess 153.

As best seen in FIG. 3, the magnets 159-161 are disposed in the recess 153 so that the magnets 159-161 are directly above the respective orifices 172-174. For example, in the illustrated embodiment, the magnet 159 corresponds to the orifice 172, the magnet 160 corresponds to the orifice 173, and the magnet 161 corresponds to the orifice 174. In that regard, the viscosity of the fluid 140 at the orifices 172-174 is controlled by the distance between the magnets 159-161 and the corresponding orifices 172-174. The greater the distance between the magnets 159-161 and the corresponding orifices 172-174, the smaller the magnetic field and the viscosity of the fluid 140 at the orifices 172-174. In contrast, the smaller the distance between the magnets 159-161 and the corresponding orifices 172-174, the greater the magnetic field and the viscosity of the fluid 140 at the orifices 172-174. To that end, the magnetic strength at the orifices 172-174 is at its strongest with the magnets 159-161 positioned directly above the orifices 172-174. Adjustment of the magnets 159-161 in a translational direction along the path of the recess 153 offsets the magnets 159-161 from being directly above the respective orifices 172-174. For example, adjusting the magnets 159-161 to the left, as viewed in FIG. 3, and along the path of the recess 153, changes the positioning of the magnets 159-161 with respect to the orifices 172-174. In particular, the distance between the magnets 159-161 and the respective orifices 172-174 increases, thereby reducing the magnetic field strength at the orifices 172-174. Similarly, adjusting the magnets 159-161 to the right, as viewed in FIG. 3, along the path of the recess 153, changes the positioning of the magnets 159-161 with respect to the orifices 172-174. In particular, the distance between the magnets 159-161 and the respective orifices 172-174 increases, thereby reducing the magnetic field strength at the orifices 172-174.

In other embodiments, the magnets 159-161 are disposed in the recess 153 in a manner so that the magnets 159-161 are independently adjustable. For example, referring to FIG. 7, the magnet 159 can be adjusted independently of the magnets 160, 161. In that regard, the position of the magnet 159 with respect to the orifice 172 is altered without changing the positions of the magnets 160, 161 with respect to the orifices 173, 174 respectively. Also in that regard, the magnet 159 can be adjusted along the path of the recess 153 and toward a posterior boundary of the recess 153 and away from the magnets 160, 161. In this instance, the distance between the magnet 159 and the orifice 172 increases, thereby reducing the magnetic field strength at the orifice 172. In that regard, the magnetic field strength at the orifice 172 is reduced while the magnetic strengths at the orifices 173, 174 remain substantially unchanged because the positions of the magnets 160, 161 have not changed. In other words, the distance between the magnets 160, 161 and the orifices 173, 174 remain constant and therefore, the magnetic field strength at the orifices 173, 174 remain relatively constant despite the change in position of the magnet 159. It is noted, however, that there is a slight decrease in the magnetic field strength at the orifices 173, 174 caused by the repositioning of the magnet 159 towards the posterior boundary of the recess 153 and toward a posterior boundary of the recess 153 and away from the magnets 160, 161.

In alternative embodiments, the relative strengths of the magnets 159-161 are different. In one instance, the relative magnetic strength of the magnet 159 is substantially greater than the relative strengths of the magnets 160, 161. In that regard, altering the position of the magnets 159 can substantially change the magnetic field strength at any one of the orifices 172-174. For example, referring again to the example discussed above with respect to adjusting the magnet 159 along the path of the recess 153 away from a posterior boundary of the recess 153 and away from the magnets 160, 161. In this instance, the distance between the magnet 159 and the orifice 172 increases, thereby reducing the magnetic field strength at the orifice 172. Moreover, the distance between the magnet 159 and the orifices 173, 174 has also increased. In that regard, since the relative strength of the magnet 159 is substantially greater than the relative strengths of the magnets 160, 161, the increase in distance between the magnet 159 and the orifices 173, 174 also reduces the magnetic field strength at the orifice 159 and at the orifices 173, 174. Discussed above are just several examples of how the magnetic strengths at the orifices 172-174 can be achieved by varying the magnetic strengths and positioning of the magnets 159-161 with respect to the orifices 172-174. It will be appreciated the by use of alternative combinations and variations of relative strengths of the magnets 159-161 and distances between the magnets 159-161 and the orifices 172-174, one skilled in the art can achieve desirable magnetic fields at the orifices 172-174.

In yet another embodiment, the magnets 159-161 are adjustable along a path defined by the height 158 of the recess 153. In that regard, and in contrast to manner of adjustment discussed above, the magnets 159-161 are adjustable in a direction generally perpendicular to the engagement and articulating surfaces 112, 109. For example, in some instances the distance between the magnets 159-161 and the respective orifices 172-174 is reduced or increased by adjusting the position of the magnets 159-161 within the recess 153 relative to the lower articulating surface 109. In that regard, the magnetic field strength at the orifices 172-174 is increased by positioning the magnets closer to the articulating surface 109. In other instances, the distance between the magnets 159-161 and the respective orifices 172-174 is increased by adjusting the magnets 159-161 in a direction toward the upper engagement surface 112. In that regard, the magnetic field strength at the orifices 172-174 is reduced. In some embodiments, the magnets 159-161 are disposed in a single biocompatible material that fits into the recess 153 such that upper surface of the material is coplanar with the engagement surface 112. In that regard, in some instances, the magnets 159-161 are disposed in the upper portion of the material, and in other instances the magnets 159-161 are disposed in the lower portion of the material. In addition, in some instances, the magnets 159-161 and the recess 153 are configured to allow adjustment in this vertical manner so that the position of the magnets 159-161 with respect to one another remain fixed. In other instances, the magnets 159-161 and the recess 153 are configured to allow adjustment of the magnets 159-161 independently of each other. In some instances, the one or more of the magnets 159-161 are disposed in a threaded engagement within the recess. In that regard, one or more of the magnets are in a housing having threads that fasten into the threaded engagement within the recess. In other instances, one or more of the magnets themselves have threads that fasten into the threaded engagement within the recess.

Now provided is an explanation of the operation of the intervertebral implant 100. As discussed above, the intervertebral implant 100 provides support and cushioning. More specifically, the damping of the intervertebral implant 100 can be adjusted in the following manner. Referring to FIG. 3, the positioning of the permanent magnets 159-161 can be adjusted as described above. By positioning the magnets 159-161 closer to the orifices 172-174, the strength of the magnetic field experienced at the orifices 172-174 increases. In turn, a stronger magnetic field at the orifices 172-172 increases the viscosity of the magnetorheological fluid disposed within the orifices. In general, the orifices 172-174 in between the bladders 163-166 mechanically restrict the magnetorheological fluid flow between the bladders 163-166 due to their reduced diameter and size relative to the bladders 163-166 themselves. However, as the viscosity of the magnetorheological fluid in the orifices 172-174 increases, the orifices in 172-174 in turn are more restrictive of the magnetorheological fluid flow between the bladders 163-166. In other words, when the strength of the magnetic field at the orifices 172-174 increases, the magnetorheological fluid disposed in the bladders 163-166 flows less easily between the bladders 163-166. Accordingly, the damping affect created by the multi-chamber support 162 is increased by increasing the strength of the magnetic fields present at each of the orifices 172-174.

On the other hand, the damping of the intervertebral implant 100 can be reduced in the opposite manner. Still referring to FIG. 3, the positioning of the permanent magnets 159-161 can be adjusted as described above. By positioning the magnets 159-161 further away from the orifices 172-174, the strength of the magnetic field experienced at the orifices 172-174 decreases. In turn, a weaker magnetic field at the orifices 172-172 decreases the viscosity of the magnetorheological fluid disposed within the orifices. As discussed above, the orifices 172-174 in between the bladders 163-166 restrict the magnetorheological fluid flow between the bladders 163-166. However, as the viscosity of the magnetorheological fluid in the orifices 172-174 decreases, the orifices in 172-174 in turn are less restrictive of the magnetorheological fluid flow between the bladders 163-166. In other words, when the strength of the magnetic field at the orifices 172-174 decreases, the magnetorheological fluid disposed in the bladders 163-166 flows more easily between the bladders 163-166. Accordingly, the damping affect created by the multi-chamber support 162 is reduced by decreasing the strength of the magnetic fields present at each of the orifices 172-174.

In some instances, regulating the flow of the magnetorheological fluid 140 between the orifices 172-174 is accomplished using alternative means. For example, an alternative embodiment of the intervertebral implant 100 focuses on contracting or expanding the orifices 172-174 that restrict the flow of the magnetorheological fluid 140 between respective bladders 163-166. In that regard, the orifices 172-174 can be controlled to increase or decrease the size of respective openings. In some instances electronics control the increase or decrease in the respective openings of the orifices 172-174. In some instances, the orifices 172-174 comprise a valve having a variable port size. In that regard, the appropriate valve dampens and/or locks the intervertebral implant. In other instances, the orifices 172-174 comprise an aperture having a variable size. In that regard, the appropriate aperture dampens and/or locks the intervertebral implant.

In yet another embodiment, generating an electromagnetic field is a substitute for the permanent magnets 159-161 of the intervertebral implant 100. In general, FIGS. 17 and 18 will be described in more detail to further explain this alternative embodiment of the present disclosure. Referring to FIG. 18, illustrated is a diagrammatic perspective view of the intervertebral implant 600 according to the embodiment of FIG. 17 of the present disclosure. The intervertebral implant 600 is similar to the intervertebral implant 100 shown in FIGS. 3 and 4. Identical or equivalent elements are identified by the same reference numerals, and the following discussion focuses primarily on the differences. In particular, the upper portion 602 differs from the upper portion 102 of the intervertebral implant 100, which can more easily be seen when referring to FIG. 18. In that regard, FIG. 18, shows a diagrammatic exploded perspective view of the upper portion 602 of the intervertebral implant 600, shown in FIG. 17. The upper portion 602 includes a support plate 604. The support plate 604 of the intervertebral implant 600 is similar to the support plate 108 of the intervertebral implant 100. Therefore, identical or equivalent elements are identified by the same reference numerals, and the following discussion focuses primarily on the differences.

In further detail, the support plate 604 includes a control electronics portion 606 and an electromagnetic field coil portion 608 for generating a magnetic field, instead of the permanent magnets 159-161 of the intervertebral implant 100.

As illustrated in FIG. 18, the electronics control portion 606 and the electromagnetic field coils portion 608 are all sized and shaped to be within a recess 610 of an engagement surface 612 so as to be substantially coplanar with the engagement surface 612 in the present embodiment. However, in some instances the electronics control portion 606 is entirely enclosed within the upper support plate 604. In other embodiments, however, the electronic control portion 606 is positioned outside of the upper support plate 604. Further, in other embodiments the electronics control portion 606 is positioned partially or entirely within the lower support plate 117. Further, in some instances electronics control portion 606 is positioned in both the upper and lower support plates 604, 117.

In more detail, the control electronics portion 606 is connected to the electromagnetic field coil portion 608. More specifically, the control electronics portion 606 includes a power supply and a controller. In this embodiment, the control electronics portion 606 and the electromagnetic field coils portion 608 are used to control and produce a magnetic field for adjusting the viscosity of the magnetorheological fluid 140. In some instances, the control electronics portion 606 produces an electric current in the electromagnetic field coils portion 608 of the upper support plate 604. In turn, the electromagnetic field coils portion 608 generates a corresponding magnetic field through the magnetorheological fluid 140. In that regard, in some instances the electronics control portion 606 determines the appropriate amount of electric current to be provided to achieve a desired viscosity at least partially based on an attribute associated with the patient's activity. For example, in some instances the electric current is determined by the electronics based on a load on the implant, an acceleration of a portion of the implant, and/or a pressure on the implant. The viscosity of the magnetorheological fluid 140 is capable of changing within a few milliseconds (generally less than 10 milliseconds) of being subjected to the magnetic field generated by the electric current from the electronics. Accordingly, in some embodiments the intervertebral implant 100 is capable of approximately real time adjustment of the stiffness and damping of the multi-chamber support 162 based on the patient's physical activities and/or attributes associated with the patient's activity.

In more detail, the electronics control portion 606 includes a processor ("processor" is understood to include microprocessors) that is connected to a power supply, a plurality of load sensors, and a plurality of microelectromechanical systems ("MEMS") devices. In some embodiments, the processor receives signals from the plurality of load sensors and/or the plurality of MEMS devices and determines the amount of voltage or current necessary to produce a magnetic field to adjust the viscosity of the magnetorheological fluid 140 to a desired level. Based on the processor's determination, the appropriate amount of current is provided from the power supply. In some instances, the processor continually monitors the signals received from the load sensors and/or the MEMS devices and continually dictates the appropriate current to be provided by the power supplies such that the multi-chamber support 162 provides the appropriate amount of stiffness and damping at all times. In that regard, in some particular aspects the stiffness and damping of the multi-chamber support 162 is adjusted within 10 ms of the processor requesting a change in the stiffness and damping. Also, in some embodiments the processor is configured to associate data from the load sensors and/or the MEMS devices with typical activities of the patient, such as walking, sitting, standing, running, laying down, kneeling, and/or other activities. Based on the associated activity as determined by the processor, a corresponding current is generated to incite the appropriate amount of stiffness damping in the multi-chamber support 162.

As mentioned, the processor determines the appropriate amount of stiffness and damping for the multi-chamber support 162 and the corresponding amount of current based on signals received from the load sensors and/or the MEMS devices. The load sensors monitor forces on the intervertebral implant 100 resulting from loads on the vertebral joint 12 and relay the corresponding loading information to the processor. The MEMS devices monitor aspects of the intervertebral implant 100 and/or vertebral joint 12 such as accelerations, rotations, and/or other motions. In that regard, the MEMS devices send the resulting data to the processor for consideration. In some embodiments, other combinations of load sensors and/or MEMS devices are utilized including only load sensors or only MEMS devices. Further still, in some instances only a single sensing element (load sensor or MEMS device) is utilized.

In order to save power and/or computing power, in some instances signals from the load sensors and/or the MEMS devices are conditioned or filtered before being sent to the processor. For example, in some instances a sufficient change in the force as measured by the load cells must occur before a signal is sent to the processor. In other instances, a threshold level of acceleration must be detected by the MEMS devices before a signal is sent to the processor. In this manner, the processor may only be utilized when a change sufficient to trigger a change in the stiffness and damping of the multi-chamber support 162 has been detected. In other instances, the load sensors and/or the MEMS devices continuously send all information to the processor for consideration.

The power supply provides the power requirements for the control electronics portion 606 and the intervertebral implant 100. In that regard, the power supply generates the electrical currents that induce the magnetic fields in the electromagnetic field coils portion 608 that change the viscosity of the magnetorheological fluid 140 in some instances. In operation, the control electronics portion 606 modulates magnetic fields produced by the electromagnetic field coils. In other instances, the power supply generates the electrical currents that change the material properties of the multi-chamber support 162 as discussed below. In the current embodiments, the power supply is a battery. In this manner the control electronics portion 606 can be internally powered. The batteries are lithium iodine batteries similar to those used for other medical implant devices such as pacemakers in some instances. It is understood that the battery can be any type of battery suitable for implantation. In some instances the battery is rechargeable. In that regard, in some specific embodiments the battery can be recharged by an external device so as to avoid the necessity of a surgical procedure to recharge the battery. For example, in one embodiment the battery is rechargeable via inductive coupling.

It is also contemplated that at least some components of the control electronics portion 606 be self-powered and not require a separate stored-energy power supply. For example, in some embodiments the load sensors and/or the MEMS devices are piezoelectric such that signals detected by these portions or other signals provide power to the sensor. In other embodiments, the control electronics portion 606 utilizes energy harvesting to recharge the power supply or store energy for use by the control electronics portion 606. Energy harvesting in this context is understood to be energy generated by the patient's motion or natural body that is captured by the intervertebral implant 100 for use in powering the control electronics portion 606. Additional and/or alternative sources of power can be utilized in other embodiments. In that regard, while a battery is illustrated, it is understood that in other embodiments a greater number of power supplies can be utilized.

Figure 19:
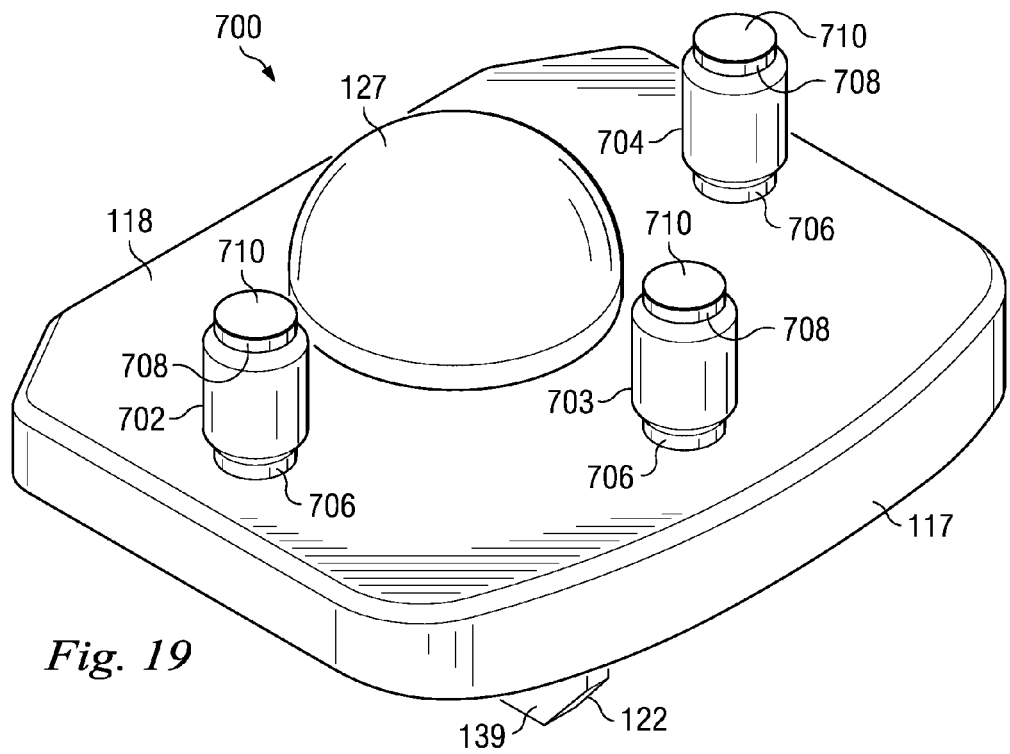
FIG. 19 is a diagrammatic perspective view of a lower portion of an intervertebral implant according to another embodiment of the present disclosure.

Referring to FIG. 19, illustrated is a diagrammatic perspective view of a lower portion 700 of an intervertebral implant according to another embodiment of the present disclosure. The lower portion 700 shown in FIG. 19 is similar to the lower portion 103 shown in FIGS. 3, 4, 9, 10, and 11. Therefore, some aspects of the lower portion 700 are identified with the same reference numerals, and are not described again here in detail. The lower portion 700 includes three support members 702, 703, 704. As shown in FIG. 19, the support members 702, 703, 704 extend from the articulating surface 118. In the illustrated embodiment, the support members 702, 703, 704 are centered about the projection 127 in a triangular like fashion. For example, the support member 702 is fixedly secured on the articulating surface 118 towards a right lateral boundary and a posterior boundary of the lower support plate 117. The support member 703 is fixedly secured to the articulating surface 118 adjacent to an anterior boundary of the lower support plate 117 and substantially centered relative to the right and left lateral boundaries of the support plate 107. Also, the support member 704 is fixedly secured on the articulating surface 118 towards a left lateral boundary and the posterior boundary of the lower support plate 117. In the current embodiment, each of the support members 702, 703, 704 are substantially the same.

Figure 20:
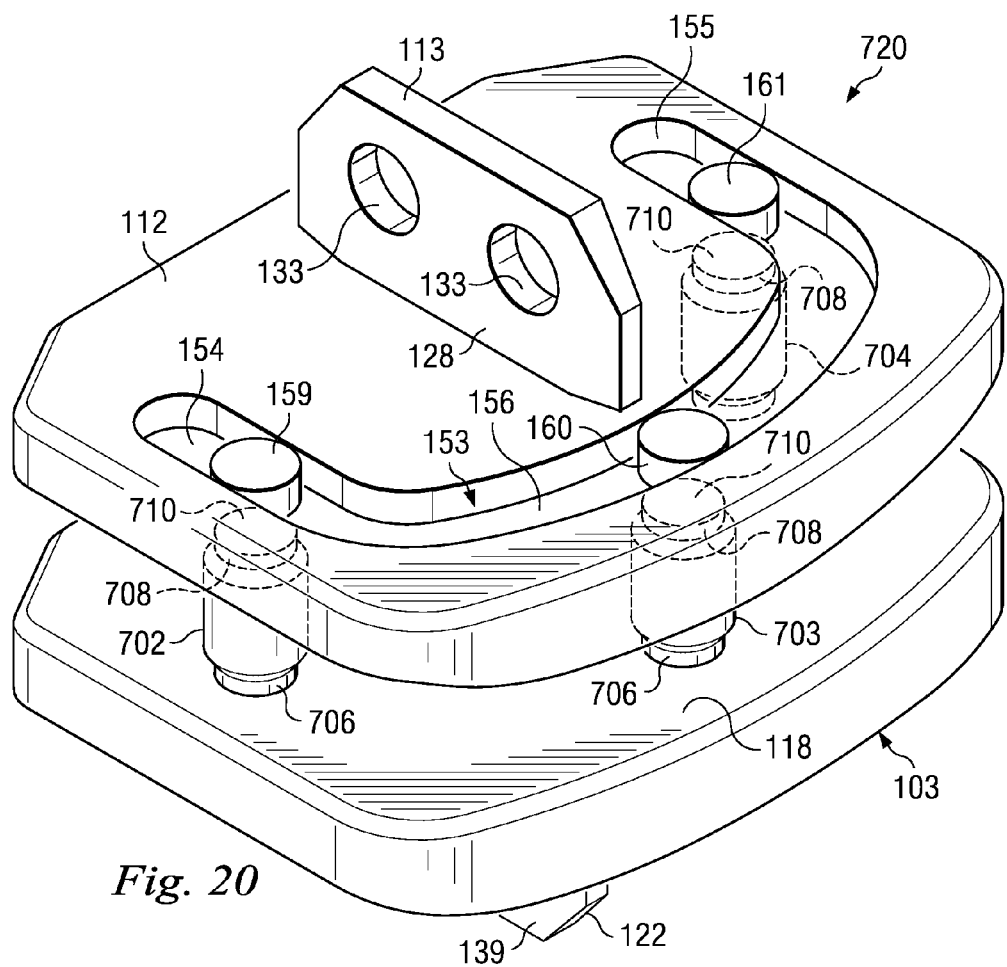
FIG. 20 is a diagrammatic perspective view of an intervertebral implant having the lower portion shown in FIG. 19, according to one embodiment of the present disclosure.

As further shown in FIG. 19, the support members 702, 703, 704 each have a cylindrical base 706 that is securely fixed to the articulating surface 118. Moreover, the support members 702, 703, 704 each have a cylindrical portion 708 that mates with and surrounds an upper portion of the base 706. The cylindrical position 708 is securely fixed to the articulating surface of an upper component (not shown) in some instances. In some instances, an end portion 710 of the support members 702, 703, 704 abuts and is secured to the articulating surface 109 of the upper support plate 108, as shown in FIG. 20 for example. The support members 702, 703, 704 provide cushioning and support.

Referring to FIG. 20, illustrated is a diagrammatic perspective view of an intervertebral implant 720 that is an alternative embodiment of an intervertebral implant of the present disclosure. The intervertebral implant 720 is similar to the intervertebral implant 100 shown in FIGS. 3 and 4. Identical or equivalent elements are identified by the same reference numerals, and the following discussion focuses primarily on the differences between the intervertebral implant 720 and the intervertebral implant 100. As shown in FIG. 20, the articulating surface 109 of the upper support plate 108 abuts the upper portion 708 of the support members 702, 703, 704. In some instances, the articulating surface 109 of the upper support plate 108 is fixedly engaged with the upper portion of the support members 702, 703, 704, while the articulating surface 118 of the lower support plate 117 is fixedly engaged with a lower portion of the support members 702, 703, 704.

Figure 21:
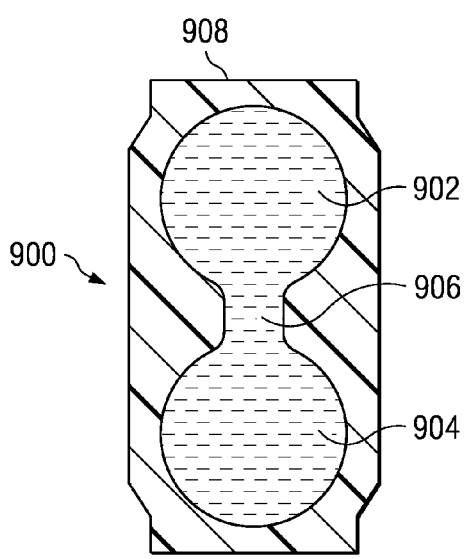
FIG. 21 is a diagrammatic cross section view of an exemplary strut for use with the intervertebral implant of FIG. 20, according to one embodiment of the present disclosure.
Figure 22:
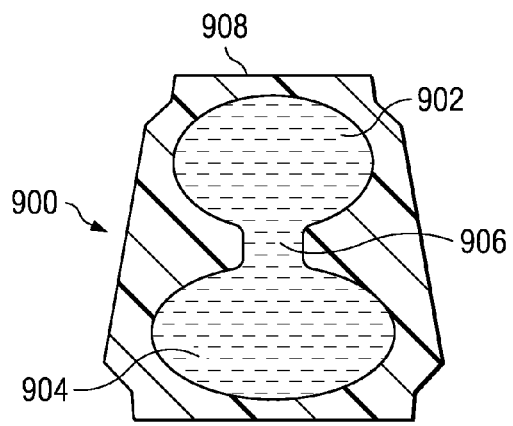
FIG. 22 is a diagrammatic cross section view of the exemplary strut similar to that of FIG. 21, but showing the strut in a compressed state.

Referring to FIGS. 21 and 22, a more detailed description of the support members 702, 703, 704 will be provided. In the current embodiment, the base 706 on the support members 702, 703, 704 are cylindrical in shape. Moreover, in this instance, the support members 702, 703, 704 are positioned so that the triangular perimeter, defined by the centers of each of the support members 702, 703, 704, is an isosceles triangle. In that regard, the spacing between the center of the support members 702, 703 is substantially equivalent to the spacing between the centers of the support members 703, 704. In other instances, the triangular perimeter is an equilateral triangle such that, the spacing between the center of the support members 702, 704 is equivalent to the spacing between the center of the support members 702, 703 and 703, 704.

In some instances, the support members 702, 703, 704 are struts. An exemplary strut 900 is shown in FIGS. 21 and 22. More specifically, referring to FIG. 21, illustrated is a diagrammatic cross-sectional view of the strut 900 for use as a support member of an intervertebral implant, such as the intervertebral implant 720 shown in FIG. 20, shown in a neutral position to one embodiment of the present disclosure. As shown, the strut 900 includes two bladders 902, 904 connected by an opening 906. In the current embodiment, the strut 900 is integrally formed of a flexible polymer material. In alternative embodiments, the strut 900 is made of one or more alternative materials such as silicon, urethane, or other biocompatible flexible material. In some instances the strut 900 houses a biocompatible fluid within its chambers 902, 904 for load bearing and motion attenuation. In some instances, the bladders 902, 904 include a magnetorheological fluid 140, as discussed above. The bladders 902, 904 have a generally circular cross-section in the neutral position, as shown. Moreover, in bladders 902, 904 are substantially equivalent in size. In some instances, the sizes and shapes of the bladders 902, 904 vary. In alternative embodiments, the bladders 902, 904 are elliptical, oval, or cubic, or any other shape suitable for containing a fluid 140 and providing cushioning and damping. Similar to the discussion above with respect to the bladders 163-166 and the respective orifices 172-174, the orifice 906 restricts the flow of the fluid 140 between the bladders 902, 904. In the neutral position of FIG. 21, the strut 900 is substantially free of compression from the upper and lower support plates 108, 117. In that regard, the sizes of the bladders 902, 904 are substantially equivalent.

Now referring to FIG. 22, shown is another diagrammatic cross-sectional view of the strut 900, shown in FIG. 21, but showing the strut deformed under compression. In this instance, some of the fluid in the bladder 902 is transferred through the orifice 906 and into the bladder 904. Moreover, as viewed in FIG. 22, the top surface 908 of the strut 900 is adjacent to the upper support plate 108 and the bottom surface 910 of the strut 900 is adjacent to the lower support plate 117. In that regard, the strut 900 allows the intervertebral implant to provide damping and cushioning, in similar fashion to the intervertebral implant 720, as explained above. In this instance, the elasticity of the bladders 902, 904 accommodate compression of the intervertebral implant. That is, under compression, some of the magnetorheological fluid 140 in the top bladder 902 is forced through the orifice 906 and into the bottom bladder 904.

Figure 24:
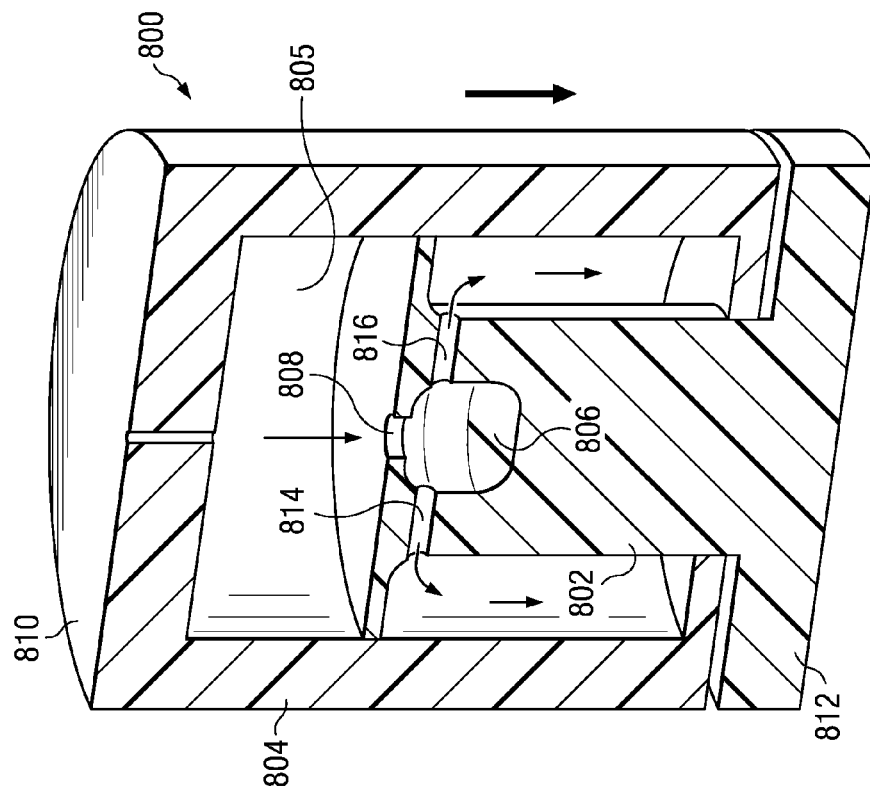
FIG. 24 is a diagrammatic cross section view of the alternative exemplary strut similar to that of FIG. 23, but showing the strut in a compressed state.
Figure 23:
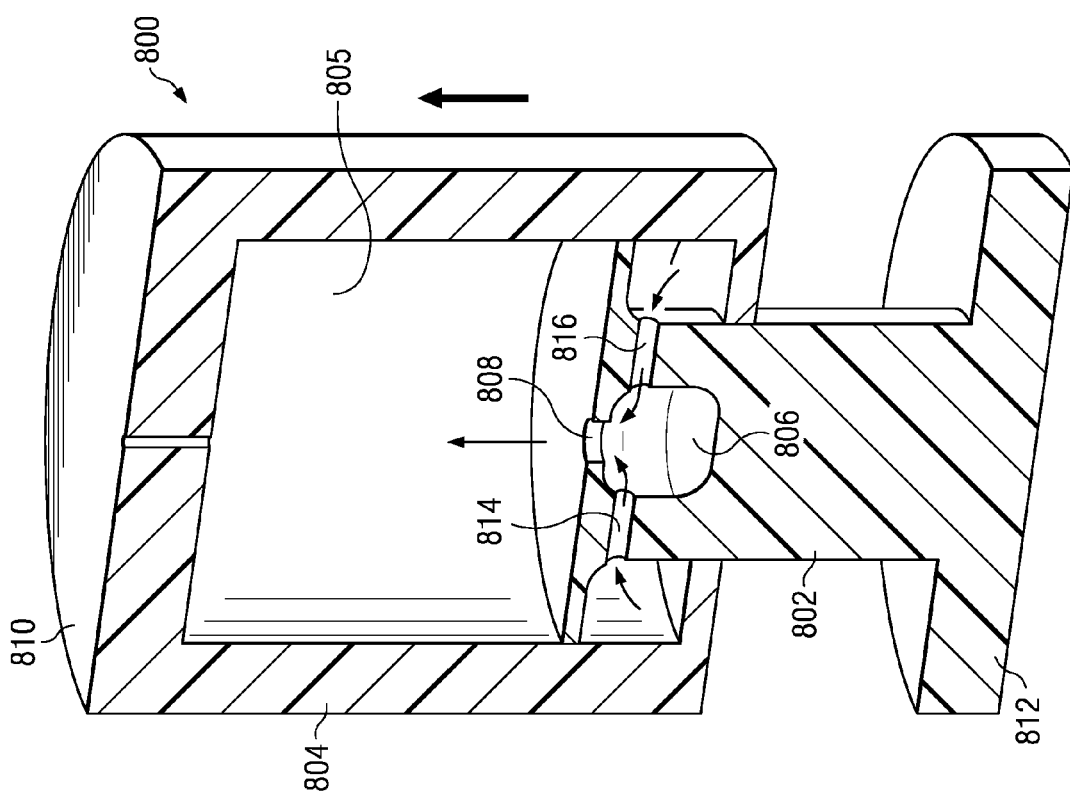
FIG. 23 is a diagrammatic cross section view of an alternative exemplary strut for use with the intervertebral implant of FIG. 20, according to one embodiment of the present disclosure.

Another type of strut is shown in FIGS. 23 and 24. More specifically, referring to FIG. 23, illustrated is a diagrammatic cross-sectional view of the strut 800 for use as a support member of an intervertebral implant, such as the intervertebral implant 720 shown in FIG. 20, shown in a neutral position to one embodiment of the present disclosure. In particular, strut 800 is a mechanical type of strut formed of generally rigid materials, in contrast to the strut 900 having elastic cavities. In that regard, the strut is formed of biocompatible metals and/or hard plastics in some instances. The strut 800 includes a piston 802 that mates with a cylinder 804. The cylinder 804 defines a cavity 805. The piston 802 and the cylinder 804 are configured in a manner so that the piston 802 fits into the cavity 805 of the cylinder 804, and can translate into and out of the cavity 805. In some instances, the cavity 805 accommodates a fluid, such as the magnetorheological fluid. The piston 802 includes a chamber 806. The chamber 806 also accommodates a fluid, such as the magnetorheological fluid. The piston 802 also includes an orifice 808 connecting the cavity 805 and the chamber 806, such that the fluid can flow there between. The orifice 808 restricts the magnetorheological fluid flow between the chamber 806 and the cavity 805 of the cylinder 804. In addition, the piston 802 includes passages 814, 816 that accommodate flow of the magnetorheological fluid between the lengths of the piston 802 and the cavity 805. In some instances, the passages 814 and 816 restrict the flow of the magnetorheological fluid 140 between the cylinder 805 and the piston 802, in a manner similar to the orifice 808, due to their reduced diameter and size relative to the chamber 806 and the cavity 805. In some instances, the passage 814 includes a valve or aperture. In some instances, the passage 816 includes a valve or aperture. In that regard, with appropriate valves and/or apertures 814, 816 connecting the adjacent chamber 806 and cavity 805, the piston 802 dampens and/or cushions the intervertebral implant. In that regard, the strut 800 and piston 802 responds to compressive loads and/or motions.

FIG. 23 shows the strut 800 when the intervertebral implant is in a neutral position. The top surface 810 of the strut 800 is substantially planar and adjacent to the upper support plate 108, shown in FIG. 20. The bottom surface 812 of the strut 800 is substantially planar and adjacent to the lower support plate 117, shown in FIG. 20. In other instances, the surfaces 810, 812 of the strut 800 can be other than substantially planar. In some instances, the strut 800 can be transposed. In that regard, the surface 810 is adjacent to the lower support plate 117, shown in FIG. 20 and the surface 812 is adjacent to the upper support plate 108.

Referring to FIG. 24, now a more detailed description of the operation of the strut 800 will be explained. FIG. 24 shows the strut 800 when the intervertebral implant is under compression between the upper and lower support plates 108, 117. In this instance, a portion of the piston 802 moves in a direction toward the top surface 810 of the strut 800 and the top surface 810 of the strut 800 moves in a direction toward the bottom surface 812 of the strut 800. In this manner, the piston 802 drives into the cavity 805 of the cylinder 804. In that regard, the magnetorheological fluid 140 maintained in the cavity 805 is displaced by the piston 802. In turn, some of the magnetorheological fluid 140 flows through the orifice 808 and into the chamber 806 and, from there, through passages 814, 816 into a lower portion of the cavity 805. The orifice 808 and passages 814, 816 restrict the flow of the magnetorheological fluid 140 between the upper portion of the cavity 805 and the chamber 806 and the lower portion of the cavity 805.

Now what follows is a brief description of the operation of the intervertebral implant 720 having one or more of the struts 800, 900. Referring back to FIG. 20, the magnets 159-161 are adjusted to change the strength of the magnetic field at the orifices 906, 808 of the respective struts 900, 800. For example, as discussed above with respect to the intervertebral implant 100, the position of the magnets 159-161 can be moved in a direction that is along the recess 153. In that instance, the distance between the magnets 159-161 and the orifices 906, 808 of the respective struts 900, 800 can be increased or decreased. For example, when the distance between the magnets 159-161 and the respective orifices are decreased, the magnetic field strength at the orifice is increased. In turn, the viscosity of the magnetorheological fluid 140 at the orifices is reduced and therefore, the orifices 906, 808 are more restrictive of the flow of the magnetorheological fluid 140 between the bladders 902, 904 in the strut 900 and between the cavity 805 and the chamber 806 in the strut 800. Alternatively, when the distance between the magnets 159-161 and the respective orifices decreased, the strength of the magnetic field at the orifices is reduced. In turn, the viscosity of the magnetorheological fluid 140 at the orifices is decreased and therefore, the orifices 906, 808 are less restrictive of the flow of the magnetorheological fluid 140 between the bladders 902, 904 in the strut 900 and between the cavity 805 and the chamber 806 in the strut 800.

Figure 17:
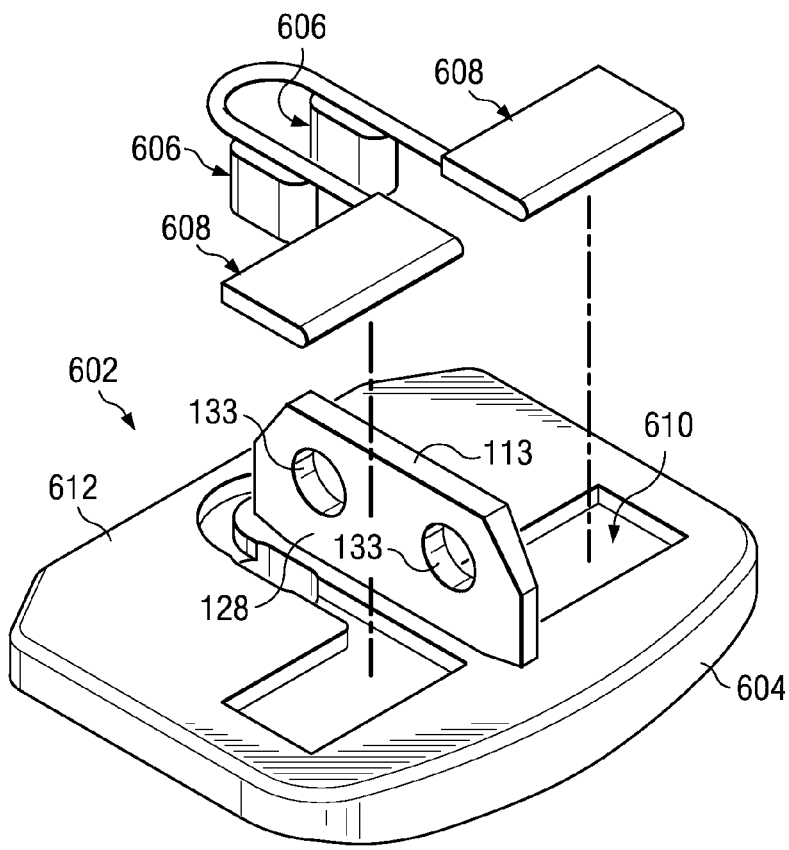
FIG. 17 is a diagrammatic perspective view of an intervertebral implant according to another embodiment of the present disclosure.
Figure 18:
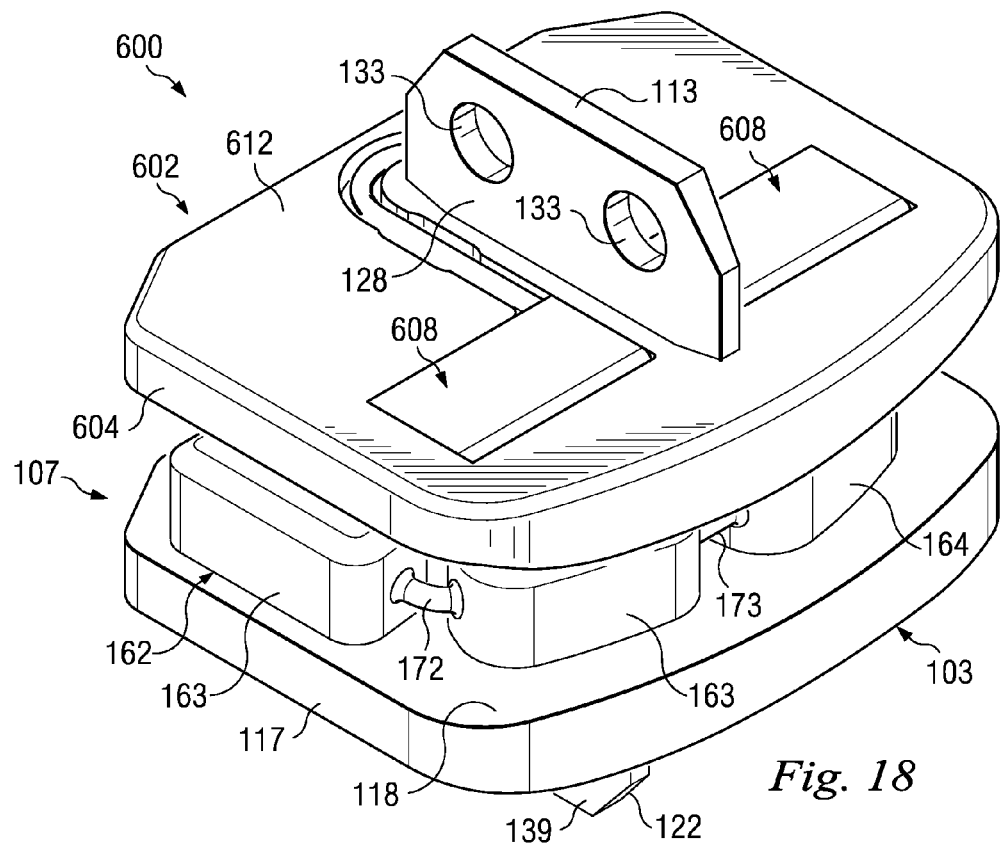
FIG. 18 is a diagrammatic exploded perspective view of an upper portion of the intervertebral implant shown in FIG. 17.

In alternative embodiments, the lower portion 103 of the intervertebral implant 600 shown in FIG. 17 is replaced with the lower portion 700 shown in FIG. 19. In that regard, the viscosity of the magnetorheological fluid 140 in each of the supports 706 changes with changes in the magnetic field strength generated my the electronics control portion 606 and the electromagnetic field coils 604. Similar to discussions above regarding alternative embodiments, in this instance the intervertebral implant provides increased cushioning and damping when the magnetic field strength is increased. In contrast, the cushioning and damping decreases when the magnetic field strength is decreased.

Figure 25:
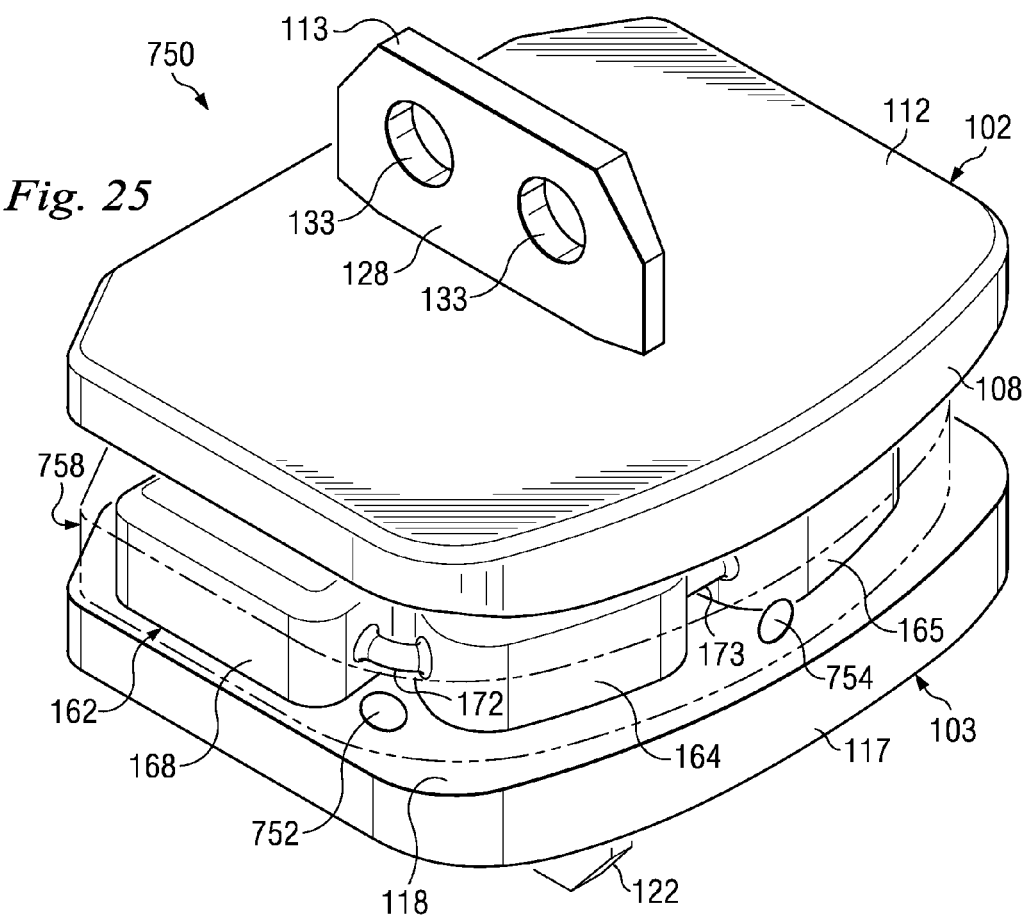
FIG. 25 is a diagrammatic perspective view of an intervertebral implant according to an alternative embodiment of the present disclosure.
Figure 26:
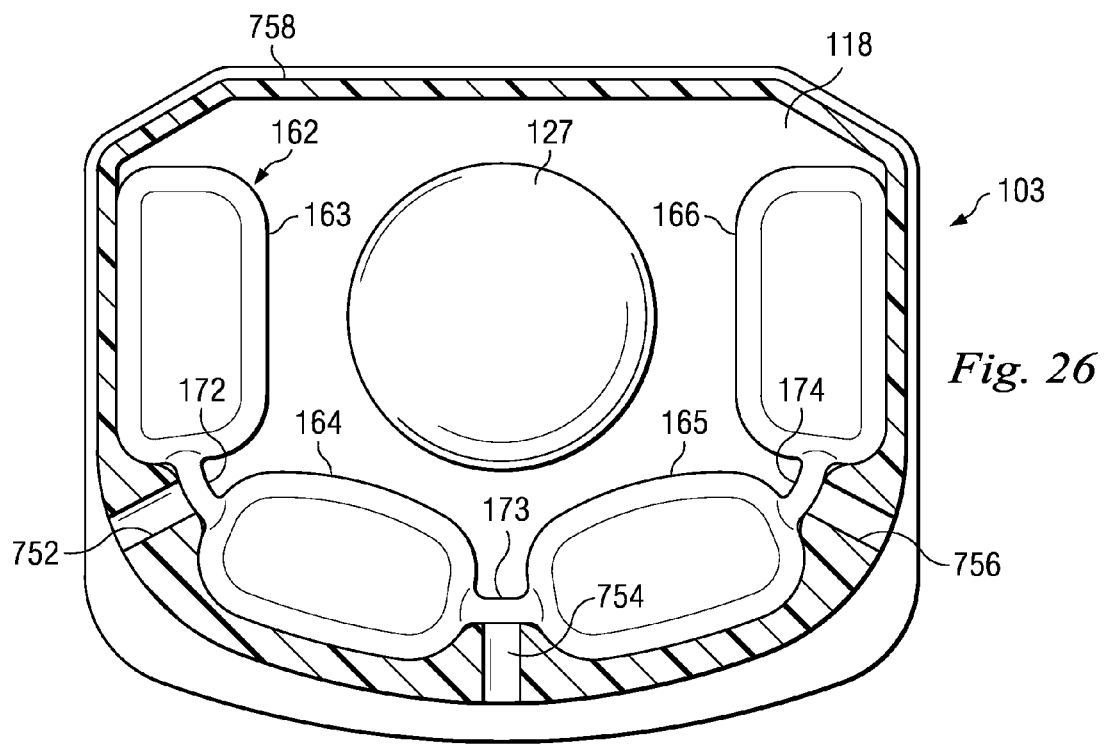
FIG. 26 is a diagrammatic top view of a lower portion of the intervertebral implant shown in FIG. 25.

Referring to FIG. 25, illustrated is a diagrammatic perspective view of an intervertebral implant 750 that is an alternative embodiment of the intervertebral implant 100. The intervertebral implant 750 is similar to the intervertebral implant 100 shown in FIGS. 3 and 4. Identical or equivalent elements are identified by the same reference numerals, and the following discussion focuses primarily on the differences. In the current embodiment, the intervertebral implant 750 has permanent magnets 752, 754, 756 recessed in a sheath 758 that circumscribes the multi-chamber support 162. Referring to FIG. 26, illustrated is a diagrammatic top phantom view of the lower portion 103 of the intervertebral implant of FIG. 25. As better seen in FIG. 26 the magnets 752, 754, 756 are disposed in the sheath 758 (shown in FIG. 25) and adjacent to the respective orifices 172-174. In the current embodiment, the magnets 752, 754, 756 (or a housing of the magnets) are threaded such that they can be screwed into sheath 758. In that regard, the distance between the magnets 752, 754, 756 and the respective orifices 172-174 can be adjusted. In alternative embodiments, the magnets 752, 754, 756 are totally embedded in the edges of the lower support plate 117, directly under the articulating surface 118. In that regard, the edges of the lower support plate 117 has threaded sockets for receiving the threaded magnets 752, 754, 756. Moreover, the length of the magnets 752, 754, 756 can protrude into the lower support plate 117 in a manner so that a portion of the magnets 752, 754, 756 are directly below the respective orifices 172-174. In some instances, the magnets 752, 754, 756 are partially embedded into the sheath 758 and the articulating surface 118 of the lower support plate 117. In alternative embodiments, the magnets 752, 754, 756 use alternative methods for fastening. For example, in some embodiments, sheath 758 and/or outer edges of the lower support plate 117 are fashioned in a ratcheting manner to adjustably receive the magnets 752, 754, 756.

The intervertebral implant 750 shown in FIG. 25 operates in a manner similar to the operation of the intervertebral implant 100 shown in FIGS. 3 and 4. To change the strength of the magnetic field that is experienced at the orifices 172-174, the magnets 752, 754, 756 are threaded either away from or into the threaded sockets in the sheath 758. For example, to increase the viscosity of the magnetorheological fluid at the orifices 172-174, the magnets 752, 754, 756 are positioned deeper into the threaded sockets in the sheath 758. In that regard, the distance between the magnets 752, 754, 756 and the respective orifices 172-174 is reduced, thereby increasing the magnetic field that is experienced at the orifices 172-175. In contrast, to reduce the viscosity of the magnetorheological fluid disposed at the orifices 172-174, the magnets 752, 754, 756 are positioned shallower in the threaded sockets in the sheath 758. In that regard, the distance between the magnets 752, 754, 756 and the respective orifices 172-175 increases, thereby reducing the magnetic field that is experienced at the orifices 172-175. In the current embodiment, the magnets 752, 754, 756 have the same magnetic strength. In addition, the magnets 752, 754, 756 are disposed into the threaded sockets in a manner so that the distances between each of magnets 752, 754, 756 and the respective orifices 172-174 is independently adjustable. This can be desirable to adjust the stiffness and damping of certain portions of the multi-chamber support 162, thereby allowing the intervertebral implant 750 to provide different cushioning and support characteristics in a particular direction or plane. In other instances, the strength of the magnetic field at the orifices 172-174 can be altered by using alternative magnets 752, 754, 756. For example, in some embodiments, the strength of at least one of the magnets 752, 754, 756 is different that the strengths of the other magnets. In that regard, when the magnets 752, 754, 756 with varying strengths are disposed in the sheath 758 at substantially similar distances from the respective orifices 172-174, the strength of the magnetic field experienced at the respective orifices 172-174 is different. In turn, the viscosity of the magnetorheological fluid at each of the orifices 172-174 is different. For example, this can be desirable to adjust the stiffness and damping of certain portions of the multi-chamber support 162, thereby allowing the intervertebral implant 750 to provide different cushioning and support characteristics in a particular direction or plane.

In some instances, the maximum amount or range of movement allowed by the intervertebral implant is varied over time. For example, in some instances it is desirable to further limit motion of the intervertebral implant in one or more directions and/or provide more rigid support to the vertebral joint over time due to the patient's physical conditions or other factors. In other instances, it is desirable to allow greater range of motion in one or more directions and/or provide less rigid support to the vertebral joint over time or after a set period of time after implantation. As discussed above, the amount of movement or range of motion allowed by the intervertebral implant is determined by the positioning of one or more magnets in some embodiments. Accordingly, in some instances the magnet(s) are positioned to facilitate the change in the range of motion of the device.

In some instances, the intervertebral implant includes memory for storing performance data for the implant. In that regard, the intervertebral implant also includes a wireless telemetry portion so that the stored data can communicate to an external receiver. In some instances, the external receiver also includes a memory unit. In that regard, the memory unit of the external receiver is adapted for multiple uses. First, the memory unit is adapted for permanent storage of the performance data obtained from the intervertebral implant. Thus, the memory unit can store data obtained at various times from the intervertebral implant so the data can later be reviewed, compared, or analyzed. Second, the memory unit can be adapted for temporary storage of performance data obtained from the implant. In this case, the memory unit will store the data until it is either discarded or transferred for permanent storage. For example, the data can be transferred from the memory unit of the external receiver via a networking interface to a network or computer for permanent storage. In some instances, such a networking interface provides a means for the external receiver to communicate with other external devices. The type of network utilized can include such communication means as telephone networks, computer networks, or any other means of communicating data electronically.

In some instances, the networking interface of the external receiver could obviate the need for the patient to even go into the doctor's office for obtaining intervertebral implant performance data. For example, the patient could utilize an external receiver to obtain the usage data from the intervertebral implant on a scheduled basis (e.g. daily, weekly, monthly, etc.). Then, utilizing the networking interface the patient could send this data to the treating medical personnel. The networking interface can be configured to directly access a communication network such as a telephone or computer network for transferring the data. It is fully contemplated that the computer network be accessible by treating medical personnel for reviewing intervertebral implant performance data of the patient without requiring the patient to make an actual visit to the doctor's office. In some instances, the networking interface is similar to the CareLink system from Medtronic, Inc.

It is also contemplated that any communication between the external receiver and the computer network can be encrypted or otherwise secured so as to protect the patient's privacy. It is also contemplated that the networking interface can be configured for communication with a separate device that is adapted for accessing the communication network. For example, the networking interface can be a USB connection. The external receiver can be connected to a personal computer via the USB connection and then the personal computer can be utilized to connect to the communication network, such as the internet, for transferring the data to a designated place where the treating doctor can receive it.

In the illustrated embodiments of the present disclosure, the intervertebral implant includes elliptical, oval, or oblong support plates as viewed from the top or bottom of the intervertebral implant (FIGS. 7 and 11 for example). In other embodiments, the support plates have other shapes, including rectangular, rectangular with curved sides, kidney shaped, heart shaped, square, oval, triangular, hexagonal, or any other shape suitable for mating with the vertebrae 14, 16. Further, in the illustrated embodiments of the present disclosure, the engagement surfaces extend relatively parallel to one another. However, in other embodiments, the engagement surfaces are angled with respect to each other to accommodate a desired lordotic or kyphotic angle. In that regard, the specific lordotic or kyphotic angle can be selected based on the level of spine in which the intervertebral implant is to be inserted. In some instances, the outer profile of the intervertebral implant is tapered, angled, or wedge shaped to create the desired lordotic or kyphotic angle. In some embodiments, the lordotic and kyphotic angles are created by utilizing one or more angled, tapered, or wedge shaped endplate assemblies. In that regard, the thickness of the support plates can vary along the length and/or width of the prosthetic device to achieve the angled orientation.

In other embodiments, the support plates have substantially planar engagement surfaces and substantially constant thicknesses, but are positioned at a lordotic or kyphotic angle due to the orientation of the supports positioned between the endplates. In some instances, the supports have a neutral position that positions the endplates in a lordotic or kyphotic angle. In some instances, the supports are biased towards the lordotic or kyphotic neutral position. In some embodiments, the relative heights of the supports are controlled by a processor and/or actuator to achieve the desired lordotic or kyphotic angle. In that regard, the processor and/or actuator will direct one or more of the supports to have an increased or decreased height relative to one or more other supports.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

What is claimed:

1. An intervertebral implant for positioning between an upper vertebra and a lower vertebra, the implant comprising:
   an upper endplate for engaging the upper vertebra;
   a lower endplate for engaging the lower vertebra;
   a damping member disposed between the upper and lower endplates, the damping member including a plurality of chambers having a material disposed therein, wherein the material has a viscosity that is dependent on a magnetic field strength; and
   a plurality of permanent magnets disposed in at least one of the upper endplate and the lower endplate, the plurality of permanent magnets generating magnetic fields for controlling the viscosity of the material disposed in the plurality of chambers of the damping member,
   wherein the at least one of the plurality of magnets is movable between a first position where the magnetic field has a first strength and a second position where the magnetic field has a second strength greater than the first strength.

2. The intervertebral implant of claim 1, wherein at least two of the plurality of chambers are connected by an opening that restricts a flow of the material between the at least two of the plurality of chambers, and wherein at least one of the plurality of magnets is disposed adjacent to the opening to produce a magnetic field through the opening in order to control the viscosity of the material within the opening.

3. The intervertebral implant of claim 2, wherein at least one of the upper endplate and the lower endplate includes a recess for receiving the at least one of the plurality of magnets disposed adjacent to the opening.

4. The intervertebral implant of claim 1, wherein each of the plurality of chambers is connected to at least one other of the plurality of chambers via an opening having a reduced inner profile relative to an inner profile of the connected chambers, the reduced inner profile of the opening restricting a flow of the material between the connected chambers, and wherein at least one of the plurality of magnets is disposed adjacent to each opening to produce a magnetic field through the opening in order to control the viscosity of the material within each opening.

5. The intervertebral implant of claim 4, wherein the plurality of magnets are disposed in a fixed orientation within a plate, and wherein at least one of the upper endplate and the lower endplate includes a recess for receiving the plate.

6. The intervertebral implant of claim 5, wherein the fixed orientation of the plurality of magnets generally corresponds to an arrangement of a plurality of openings connecting the plurality of chambers such that each of the plurality of magnets is positioned adjacent one of the plurality of openings.

7. The intervertebral implant of claim 6, wherein the plate is slidable along the recess so that a distance between each of the plurality of magnets and the corresponding openings is variable in order to adjust a strength of the magnetic field through each opening.

8. A prosthetic device for a spinal joint, comprising:
a first component sized and shaped for engaging a first bony portion of the spinal joint;
a second component sized and shaped for engaging a second bony portion of the spinal joint, the second component in articulating engagement with the first component; and
a bladder system positioned between the first and second engagement components, the bladder system comprising a plurality of flexible bladders and at least one orifice extending from each of the plurality of bladders to at least one other of the plurality of bladders, wherein each of the plurality of bladders contains a fluid and wherein the at least one orifice has a reduced inner diameter relative to an inner diameter of the plurality of bladders such that a flow of fluid between the bladders connected by the at least one orifice is restricted.

9. The prosthetic device of claim 8, wherein the first and second components are in articulating engagement via a ball-and-socket joint and wherein the bladder system generally surrounds the ball-and-socket joint.

10. The prosthetic device of claim 8, wherein the fluid is selected from the group of biocompatible fluids comprising water, saline, polyethylene glycol, glycerol, plasma extender, and hydrocarbon solvents.

11. The prosthetic device of claim 8, wherein the fluid is selected from the group of biocompatible fluids comprising magnetorheologic fluids, ferrofluids, and electrorheologic fluids.

12. The prosthetic device of claim 11, further comprising at least one field generating component for defining a rheological behavior of the fluid.

13. A spinal implant, comprising:
a first component having a first engagement surface for engaging a first vertebra;
a second component having a second engagement surface for engaging a second vertebra; and
a damping member positioned between the first and second components, the damping member comprising at least two chambers connected by at least one opening, a fluid is disposed within the at least two chambers of the damping member such that compression of the first and second components towards one another causes the fluid to be displaced from one of the at least two chambers to another of the at least two chambers through the at least one opening, the at least one opening having a reduced size relative to the at least two chambers to restrict the flow of the fluid between the at least two chambers and provide a dampening effect,
wherein the damping member comprises a strut such that a first portion of the strut is fixedly attached to the first component and a second portion of the strut is fixedly attached to the second component.

14. The spinal implant of claim 13, wherein fluid comprises magnetically sensitive particles such that a rheologic behavior of the fluid is dependent on a magnetic field passing through the fluid.

15. The spinal implant of claim 14, further comprising a magnetic source for generating a magnetic field for controlling the rheologic behavior of the fluid.

16. The spinal implant of claim 15, wherein the magnetic source is at least one permanent magnet.

17. The prosthetic device of claim 15, wherein the magnetic source comprises electronics that produce an electromagnetic field.

* * * * *